(12) United States Patent
Rosati et al.

(10) Patent No.: US 10,993,845 B2
(45) Date of Patent: *May 4, 2021

(54) PROCESS FOR MAKING AN ABSORBENT ARTICLE COMPRISING A TOPSHEET/ACQUISITION LAYER LAMINATE

(71) Applicant: The Procter & Gamble Company, Cincinnati, OH (US)

(72) Inventors: Rodrigo Rosati, Frankfurt Am Main (DE); Jill Marlene Orr, Liberty Township, OH (US); Adrien Greiner, Frankfurt Am Main (DE); James T. Knapmeyer, Cincinnati, OH (US); Aniruddha Chatterjee, Kelkheim (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/879,860

(22) Filed: May 21, 2020

(65) Prior Publication Data

US 2020/0306097 A1    Oct. 1, 2020

Related U.S. Application Data

(63) Continuation of application No. 16/256,264, filed on Jan. 24, 2019, now Pat. No. 10,687,987, which is a
(Continued)

(51) Int. Cl.
*A61F 13/51* (2006.01)
*A61F 13/15* (2006.01)
(Continued)

(52) U.S. Cl.
CPC .. *A61F 13/15699* (2013.01); *A61F 13/15203* (2013.01); *A61F 13/15707* (2013.01);
(Continued)

(58) Field of Classification Search
CPC .......... A61F 13/15699; A61F 13/15203; A61F 13/15723; A61F 13/45; A61F 13/51; A61F 13/51104
See application file for complete search history.

(56) References Cited

U.S. PATENT DOCUMENTS

| 4,323,068 A | 4/1982 | Aziz |
| 5,338,766 A | 8/1994 | Phan et al. |

(Continued)

FOREIGN PATENT DOCUMENTS

| EP | 1184075 | 9/2000 |
| EP | 1283028 | 2/2003 |

(Continued)

OTHER PUBLICATIONS

International Search Report and Written Opinion, PCT/US2015/048303, dated Nov. 17, 2015.
(Continued)

*Primary Examiner* — Jeffry H Aftergut
*Assistant Examiner* — Jaeyun Lee
(74) *Attorney, Agent, or Firm* — George H. Leal

(57) ABSTRACT

A process of making an absorbent article is disclosed. A liquid permeable topsheet web extending substantially continuously in a machine direction a backsheet web, and an intermediate layer are provided. The topsheet web has first and second surfaces. The backsheet web extends substantially continuously in the machine direction. The intermediate layer has a first and second surface. The topsheet and intermediate layer are aligned in a face to face relationship such that the second surface of the topsheet in in contact with the first surface of the intermediate layer and simultaneously mechanically deformed which combines the topsheet with the intermediate layer. The topsheet web and intermediate layer are nested together such that a majority of
(Continued)

the three-dimensional protrusions formed in the topsheet web coincide with and fit together with a majority of the three-dimensional protrusions formed in the intermediate layer to provide a topsheet/intermediate layer laminate web having three-dimensional protrusions.

17 Claims, 21 Drawing Sheets

Related U.S. Application Data continuation of application No. 14/844,343, filed on Sep. 3, 2015, now Pat. No. 10,226,385.

(60) Provisional application No. 62/210,005, filed on Aug. 26, 2015, provisional application No. 62/210,057, filed on Aug. 26, 2015, provisional application No. 62/210,014, filed on Aug. 26, 2015, provisional application No. 62/210,020, filed on Aug. 26, 2015, provisional application No. 62/049,406, filed on Sep. 12, 2014, provisional application No. 62/049,521, filed on Sep. 12, 2014, provisional application No. 62/049,401, filed on Sep. 12, 2014, provisional application No. 62/049,403, filed on Sep. 12, 2014, provisional application No. 62/049,392, filed on Sep. 12, 2014, provisional application No. 62/049,516, filed on Sep. 12, 2014, provisional application No. 62/049,404, filed on Sep. 12, 2014, provisional application No. 62/049,408, filed on Sep. 12, 2014, provisional application No. 62/049,397, filed on Sep. 12, 2014.

(51) Int. Cl.

| | | |
|---|---|---|
| *A61F 13/511* | (2006.01) | |
| *A61F 13/512* | (2006.01) | |
| *A61F 13/536* | (2006.01) | |
| *A61F 13/537* | (2006.01) | |
| *A61F 13/513* | (2006.01) | |
| *A61F 13/53* | (2006.01) | |
| *A61F 13/534* | (2006.01) | |
| *A61F 13/45* | (2006.01) | |
| *A61F 13/551* | (2006.01) | |
| *A61F 13/535* | (2006.01) | |
| *A61F 13/538* | (2006.01) | |
| *A61F 13/539* | (2006.01) | |
| *A61F 13/84* | (2006.01) | |
| *A61F 13/42* | (2006.01) | |

(52) U.S. Cl.
CPC ........ *A61F 13/15723* (2013.01); *A61F 13/45* (2013.01); *A61F 13/51* (2013.01); *A61F 13/511* (2013.01); *A61F 13/513* (2013.01); *A61F 13/5116* (2013.01); *A61F 13/5121* (2013.01); *A61F 13/51104* (2013.01); *A61F 13/51108* (2013.01); *A61F 13/51394* (2013.01); *A61F 13/53* (2013.01); *A61F 13/534* (2013.01); *A61F 13/535* (2013.01); *A61F 13/536* (2013.01); *A61F 13/537* (2013.01); *A61F 13/551* (2013.01); *A61F 13/55105* (2013.01); *A61F 13/55115* (2013.01); *A61F 13/55145* (2013.01); *A61F 2013/15284* (2013.01); *A61F 2013/15365* (2013.01); *A61F 2013/15463* (2013.01); *A61F 2013/15715* (2013.01); *A61F 2013/421* (2013.01); *A61F 2013/427* (2013.01); *A61F 2013/4568* (2013.01); *A61F 2013/4587* (2013.01); *A61F 2013/51002* (2013.01); *A61F 2013/51007* (2013.01); *A61F 2013/51009* (2013.01); *A61F 2013/51023* (2013.01); *A61F 2013/51026* (2013.01); *A61F 2013/51092* (2013.01); *A61F 2013/51147* (2013.01); *A61F 2013/51355* (2013.01); *A61F 2013/51377* (2013.01); *A61F 2013/5307* (2013.01); *A61F 2013/530007* (2013.01); *A61F 2013/5386* (2013.01); *A61F 2013/5395* (2013.01); *A61F 2013/530131* (2013.01); *A61F 2013/530175* (2013.01); *A61F 2013/53472* (2013.01); *A61F 2013/530481* (2013.01); *A61F 2013/530489* (2013.01); *A61F 2013/530664* (2013.01); *A61F 2013/530715* (2013.01); *A61F 2013/53908* (2013.01); *A61F 2013/8497* (2013.01)

(56) References Cited

U.S. PATENT DOCUMENTS

| | | | |
|---|---|---|---|
| 5,518,801 | A | 5/1996 | Chappell et al. |
| 5,599,335 | A | 2/1997 | Goldman et al. |
| 5,628,097 | A | 5/1997 | Benson et al. |
| 5,804,021 | A | 9/1998 | Abuto |
| 5,888,607 | A | 3/1999 | Seth et al. |
| 5,938,650 | A | 8/1999 | Baer et al. |
| 6,136,124 | A | 10/2000 | Wagner |
| 6,274,218 | B1 | 8/2001 | Shimizu |
| 6,319,239 | B1 * | 11/2001 | Daniels ................. A61F 13/539 604/378 |
| 6,344,102 | B1 | 2/2002 | Wagner |
| 6,395,957 | B1 | 5/2002 | Chen et al. |
| 6,440,564 | B1 | 8/2002 | McLain et al. |
| 6,610,904 | B1 | 8/2003 | Thomas et al. |
| 6,641,902 | B1 | 11/2003 | Kobayashi et al. |
| 6,685,686 | B2 | 2/2004 | Hermansson et al. |
| 6,700,036 | B2 | 3/2004 | Thomas et al. |
| 6,733,626 | B2 | 5/2004 | Ruthven et al. |
| 6,739,024 | B1 | 5/2004 | Wagner |
| 6,818,802 | B2 | 11/2004 | Takai et al. |
| 6,887,349 | B2 | 5/2005 | Ruthven et al. |
| 7,037,406 | B2 | 5/2006 | Kershaw et al. |
| 7,060,344 | B2 | 6/2006 | Pourdeyhimi et al. |
| 7,172,801 | B2 | 2/2007 | Hoying |
| 7,182,838 | B2 | 2/2007 | Ruthven et al. |
| 7,267,860 | B2 | 9/2007 | Toyoshima et al. |
| 7,294,231 | B2 | 11/2007 | Kershaw et al. |
| 7,297,226 | B2 | 11/2007 | Schulz |
| 7,326,322 | B2 | 2/2008 | Ruthven et al. |
| 7,410,683 | B2 | 8/2008 | Curro |
| 7,468,114 | B2 | 12/2008 | Sato et al. |
| 7,531,062 | B2 | 5/2009 | Kershaw et al. |
| 7,553,532 | B2 | 6/2009 | Turner |
| 7,648,752 | B2 | 1/2010 | Hoying et al. |
| 7,678,034 | B2 | 3/2010 | Wilhelm |
| 7,682,686 | B2 | 3/2010 | Curro et al. |
| 7,687,679 | B2 | 3/2010 | Mishima |
| 7,799,176 | B2 | 9/2010 | Schulz |
| 7,842,849 | B2 | 11/2010 | Datta |
| 7,857,941 | B2 | 12/2010 | Ruthven et al. |
| 7,951,127 | B2 | 5/2011 | Sanabria et al. |
| 8,142,617 | B2 | 3/2012 | Ruthven et al. |
| D662,326 | S | 6/2012 | Shanbhag |
| 8,231,377 | B2 | 7/2012 | Wittner et al. |
| 8,241,543 | B2 | 8/2012 | Odonnell |
| 8,287,694 | B2 | 10/2012 | Schulz |
| 8,304,600 | B2 | 11/2012 | Noda et al. |
| 8,313,473 | B2 | 11/2012 | Datta |
| D672,152 | S | 12/2012 | Shanbhag |
| 8,393,374 | B2 | 3/2013 | Sato |
| 8,535,481 | B2 | 9/2013 | Schulz |
| 8,574,209 | B2 | 11/2013 | Nishitani et al. |
| 8,585,958 | B2 | 11/2013 | Gray |
| 8,617,449 | B2 | 12/2013 | Baker |

(56) References Cited

U.S. PATENT DOCUMENTS

| | | |
|---|---|---|
| 9,198,809 B2 | 12/2015 | Hammons et al. |
| 2002/0004654 A1 | 1/2002 | Daniels et al. |
| 2002/0133131 A1 | 9/2002 | Rangachari et al. |
| 2002/0193776 A1* | 12/2002 | Fernfors ........... A61F 13/15756 604/389 |
| 2003/0195487 A1 | 10/2003 | Thomas |
| 2003/0211802 A1 | 11/2003 | Keck et al. |
| 2004/0002688 A1 | 1/2004 | Thomas et al. |
| 2004/0087919 A1* | 5/2004 | Tanaka ................. A61F 13/505 604/327 |
| 2004/0229008 A1 | 11/2004 | Hoying |
| 2004/0265534 A1 | 12/2004 | Curro et al. |
| 2005/0008825 A1 | 1/2005 | Casey |
| 2005/0283129 A1* | 12/2005 | Hammons ........... A61F 13/8405 604/384 |
| 2006/0111684 A1 | 5/2006 | Berba |
| 2006/0194027 A1 | 8/2006 | Pourdeyhimi |
| 2006/0286343 A1 | 12/2006 | Curro |
| 2007/0212966 A1 | 9/2007 | Wittner et al. |
| 2008/0221538 A1 | 9/2008 | Zhao et al. |
| 2008/0227356 A1 | 9/2008 | Poruthoor |
| 2009/0030390 A1 | 1/2009 | Hammons |
| 2010/0024974 A1 | 2/2010 | Narita |
| 2010/0028621 A1 | 2/2010 | Byrne |
| 2010/0036338 A1 | 2/2010 | Hammons |
| 2010/0247844 A1 | 9/2010 | Curro |
| 2010/0297377 A1 | 11/2010 | Mcneil |
| 2011/0073513 A1 | 3/2011 | Weisman et al. |
| 2011/0094669 A1 | 4/2011 | Oetjen |
| 2011/0125120 A1 | 5/2011 | Nishitani |
| 2011/0260371 A1 | 10/2011 | Arora |
| 2012/0064298 A1 | 3/2012 | Orr |
| 2012/0136329 A1 | 5/2012 | Carney |
| 2012/0234475 A1 | 9/2012 | Paldey |
| 2012/0238984 A1 | 9/2012 | Paldey |
| 2013/0165883 A1 | 6/2013 | Kimura |
| 2013/0309439 A1 | 11/2013 | Close |
| 2014/0039434 A1 | 2/2014 | Xu |
| 2014/0052088 A1 | 2/2014 | Weisman et al. |
| 2014/0054827 A1 | 2/2014 | Mullane |
| 2014/0121621 A1 | 5/2014 | Kirby |
| 2014/0121623 A1 | 5/2014 | Kirby |
| 2014/0121624 A1 | 5/2014 | Kirby |
| 2014/0121625 A1 | 5/2014 | Kirby |
| 2014/0121626 A1 | 5/2014 | Finn et al. |
| 2014/0163500 A1 | 6/2014 | Roe |
| 2014/0163501 A1 | 6/2014 | Ehrnsperger |
| 2014/0170367 A1 | 6/2014 | Turner |
| 2014/0276517 A1 | 9/2014 | Chester et al. |
| 2014/0367290 A1 | 12/2014 | Nomoto |
| 2015/0073366 A1 | 3/2015 | Ehrnsperger |

FOREIGN PATENT DOCUMENTS

| | | |
|---|---|---|
| EP | 861646 | 5/2003 |
| EP | 1208828 | 7/2005 |
| EP | 1774940 A1 | 4/2007 |
| EP | 1787611 | 5/2007 |
| EP | 2554730 | 2/2013 |
| EP | 1982013 | 6/2013 |
| EP | 2437708 | 9/2013 |
| EP | 2277485 | 5/2014 |
| EP | 1842513 B1 | 9/2014 |
| JP | 02055058 | 8/1988 |
| JP | 3124190 | 9/1994 |
| JP | 3868880 B2 | 10/2002 |
| JP | 3880502 B2 | 10/2002 |
| JP | 4282428 B2 | 9/2003 |
| JP | 4974524 B2 | 12/2005 |
| JP | 4901425 B2 | 11/2006 |
| JP | 5103100 B2 | 9/2007 |
| JP | 5074174 B2 | 12/2007 |
| JP | 2009172354 | 4/2008 |
| JP | 4184253 B2 | 9/2008 |
| JP | 2013074978 | 9/2011 |
| JP | 2011200446 A | 10/2011 |
| JP | 2012010884 A | 1/2012 |
| JP | 4931580 B2 | 5/2012 |
| JP | 5099782 | 12/2012 |
| JP | 5148182 B2 | 12/2012 |
| JP | 5268416 B2 | 5/2013 |
| JP | 2013126455 | 6/2013 |
| JP | 5319367 B2 | 7/2013 |
| JP | 2013169388 A | 9/2013 |
| WO | WO9301781 A1 | 2/1993 |
| WO | WO9827904 A1 | 7/1998 |
| WO | WO200029199 | 5/2000 |
| WO | WO200038604 | 7/2000 |
| WO | WO0174281 A1 | 10/2001 |
| WO | WO2002024133 A1 | 3/2002 |
| WO | WO2004029349 | 4/2004 |
| WO | WO2004098869 A1 | 11/2004 |
| WO | WO2006007149 A1 | 1/2006 |
| WO | WO2007001270 A1 | 1/2007 |
| WO | WO2007116944 A1 | 10/2007 |
| WO | WO2008146594 | 4/2008 |
| WO | WO2009139255 | 1/2009 |
| WO | WO20100074205 | 7/2010 |
| WO | WO2010118272 | 10/2010 |
| WO | WO2011142272 A1 | 11/2011 |
| WO | WO2012176656 A1 | 12/2012 |
| WO | WO2013047890 A1 | 4/2013 |
| WO | WO2013077074 | 5/2013 |
| WO | WO2013099463 A1 | 7/2013 |
| WO | WO2013147222 A1 | 10/2013 |
| WO | WO2013175360 A1 | 11/2013 |
| WO | WO2014084066 A1 | 6/2014 |

OTHER PUBLICATIONS

All Office Actions for U.S. Appl. No. 16//256,264, filed Jan. 24, 2019.

All Office Actions for U.S. Appl. No. 14/844,343, filed Sep. 3. 2015.

* cited by examiner

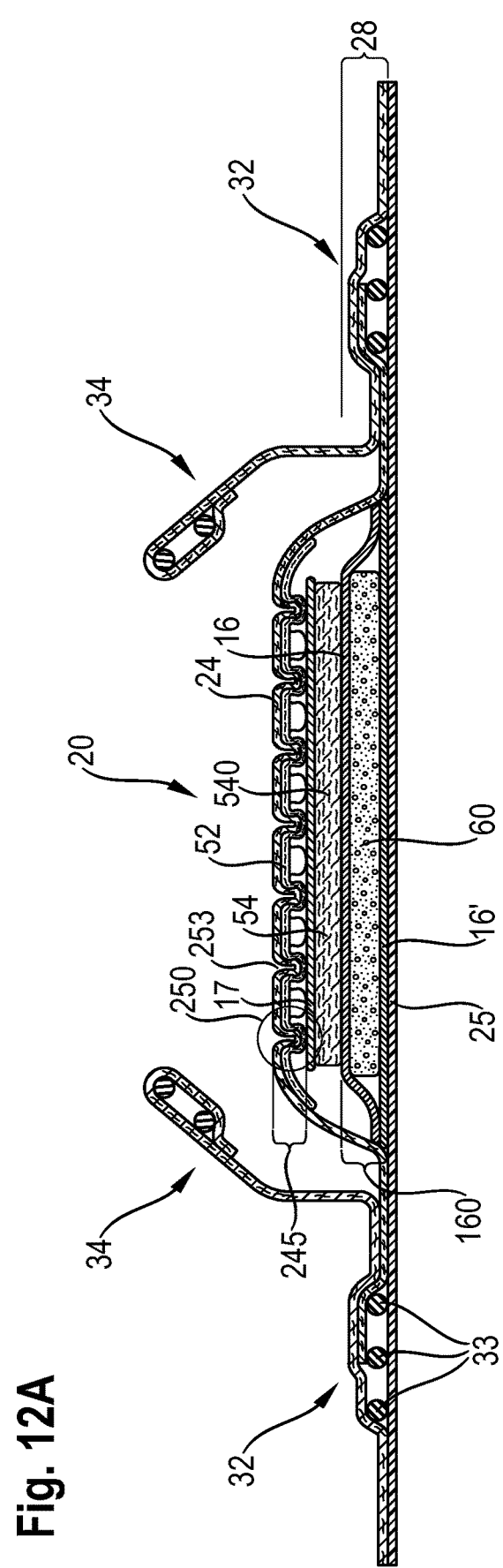

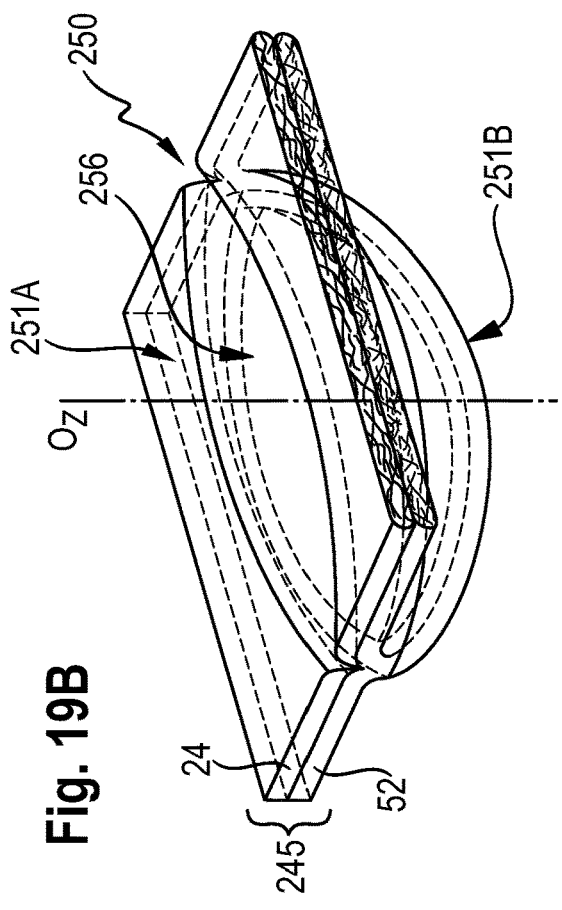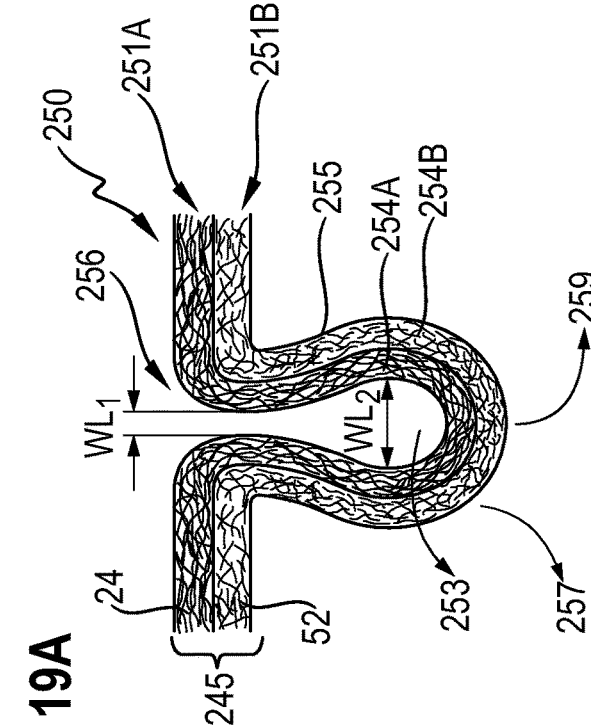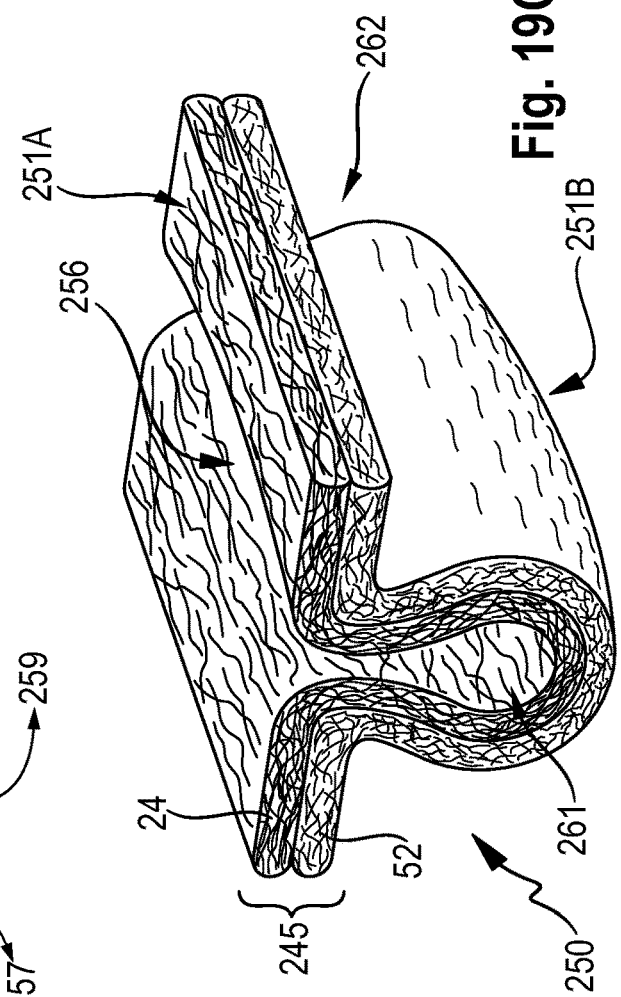
Fig. 19A
Fig. 19B
Fig. 19C

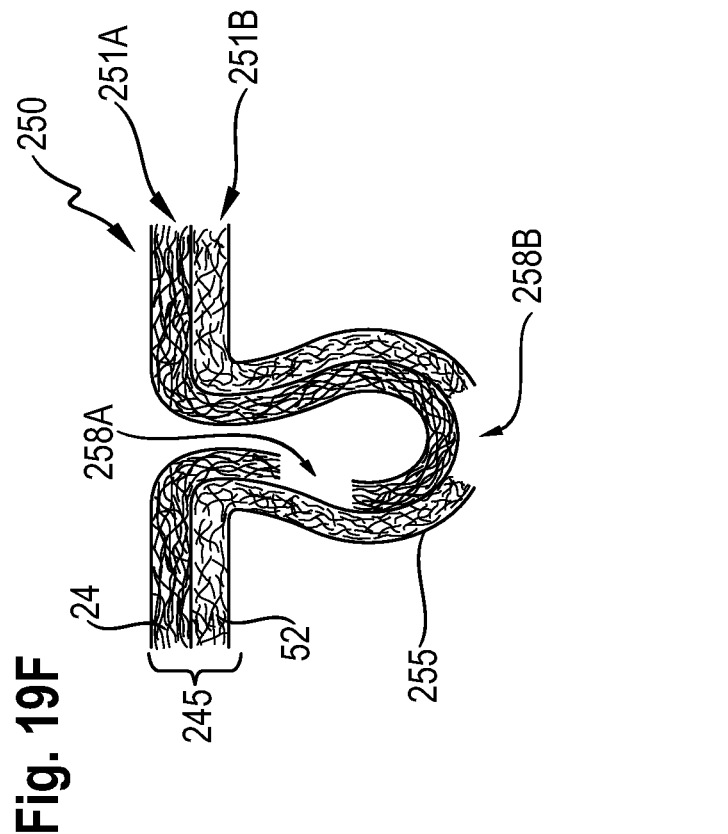
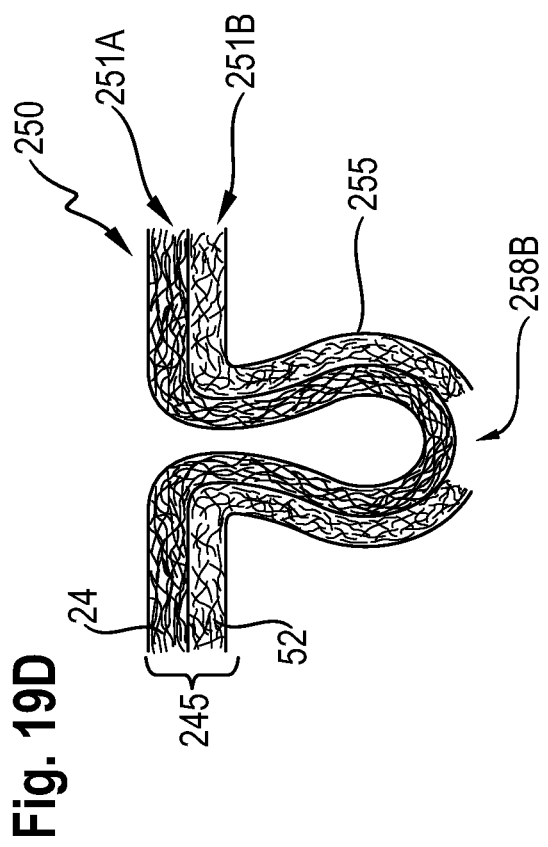
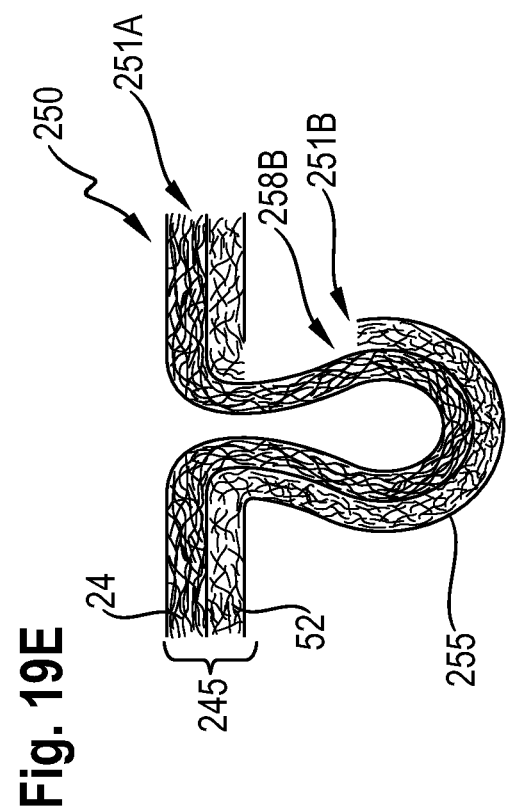

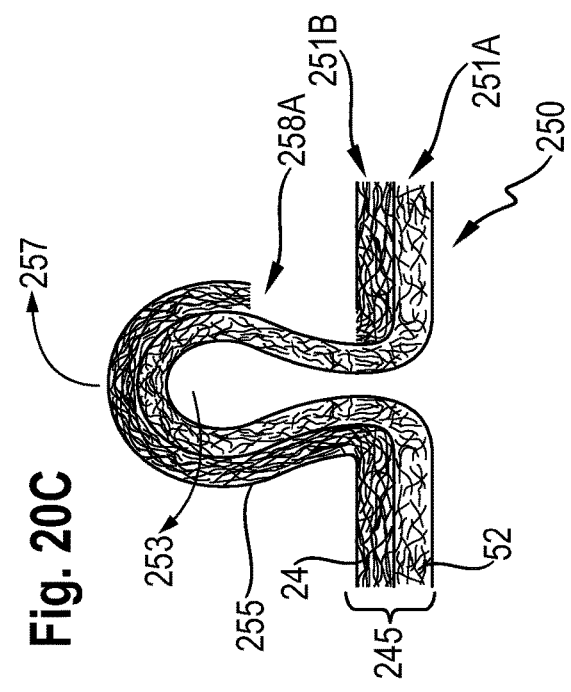
Fig. 20C
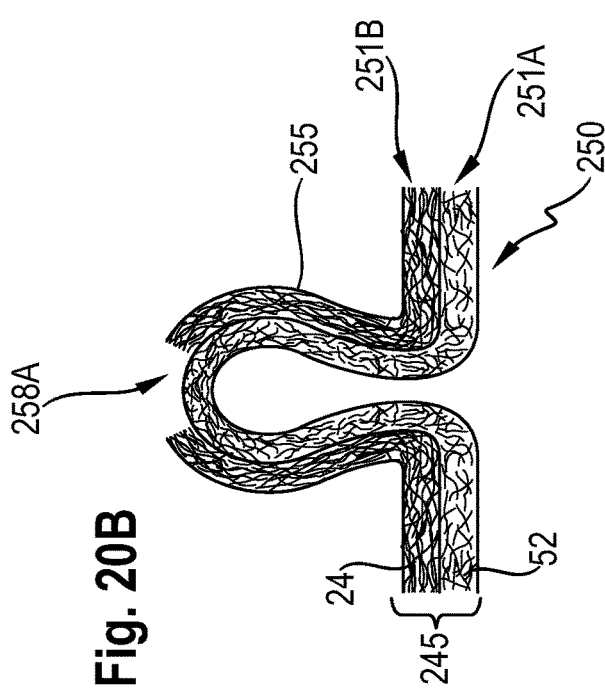
Fig. 20D
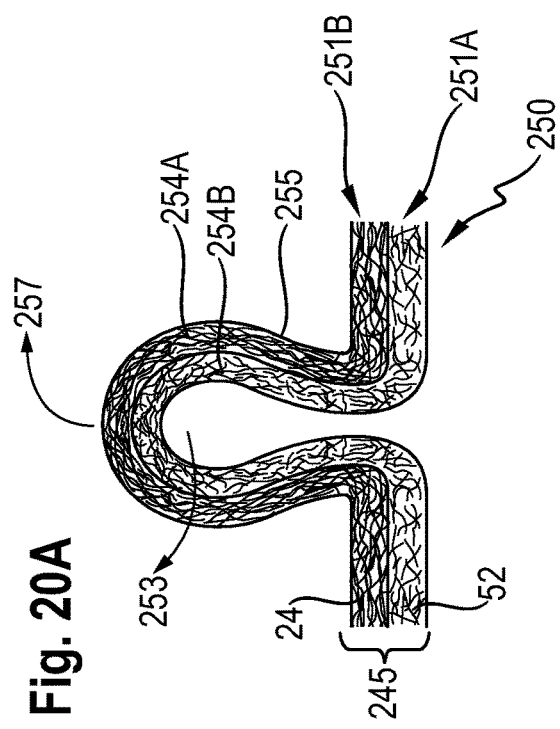
Fig. 20A
Fig. 20B

PROCESS FOR MAKING AN ABSORBENT ARTICLE COMPRISING A TOPSHEET/ACQUISITION LAYER LAMINATE

FIELD OF THE INVENTION

A process of making an absorbent article comprising a topsheet/acquisition layer laminate is provided. Specifically, a process of making an absorbent article comprising a topsheet/acquisition layer laminate, a dry-laid fibrous structure and an optional carrier layer is provided.

BACKGROUND OF THE INVENTION

An absorbent article typically comprises a topsheet, a backsheet, and an absorbent core disposed between the topsheet and the backsheet. The absorbent article includes an acquisition layer and optionally a distribution layer. The acquisition layer is able to receive the liquid bodily exudates from the topsheet in order to temporary store them. Then, the distribution layer can receive the liquid bodily exudates from the acquisition layer and distribute and transfer them to the absorbent core in order to make efficient the use of the absorbent core. Such absorbent articles exhibit satisfactory fluid handling properties.

Three-dimensional topsheets have been developed; see for example U.S. Patent application US 2014/0121625 A1.

There still remains a need to further improve three-dimensional topsheets.

There is a need to develop a method to prepare a skin facing layer having a three-dimensional structure for an absorbent article providing improved fluid handling properties e.g. less rewet on the skin facing layer, while the physical and perceptional comfort of the wearer are still met.

There is also a need to produce a skin facing layer having a three-dimensional structure in order to reduce the contact of the liquid bodily exudates with the skin of the wearer. It is desirable as well that the skin facing layer shall provide a softness/cushiness feeling for the caregiver and the wearer.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

FIG. 12A is a transversal cross-section of the diaper of FIG. 11;

FIG. 19A is a schematic view of a three-dimensional protrusion of the topsheet/acquisition layer laminate obtained with the apparatus shown in FIG. 17;

FIG. 19B is a perspective view of a three-dimensional protrusion of the topsheet/acquisition layer laminate shown in FIG. 19A;

FIG. 19C is another perspective view of a three-dimensional protrusion of the topsheet/acquisition layer laminate shown in FIG. 19A;

FIG. 19D is a schematic view of a three-dimensional protrusion of the topsheet/acquisition layer laminate obtained with the apparatus shown in FIG. 17;

FIG. 19E is a schematic view of a three-dimensional protrusion of the topsheet/acquisition layer laminate obtained with the apparatus shown in FIG. 17;

FIG. 19F is a schematic view of a three-dimensional protrusion of the topsheet/acquisition layer laminate obtained with the apparatus shown in FIG. 17;

FIG. 20A is a schematic view of a three-dimensional protrusion of the topsheet/acquisition layer laminate obtained with the apparatus shown in FIG. 17;

FIG. 20B is a schematic view of a three-dimensional protrusion of the topsheet/acquisition layer laminate obtained with the apparatus shown in FIG. 17;

FIG. 20C is a schematic view of a three-dimensional protrusion of the topsheet/acquisition layer laminate obtained with the apparatus shown in FIG. 17;

FIG. 20D is a schematic view of a three-dimensional protrusion of the topsheet/acquisition layer laminate obtained with the apparatus shown in FIG. 17.

DETAILED DESCRIPTION OF THE INVENTION

Definition of Terms

Figure 1:
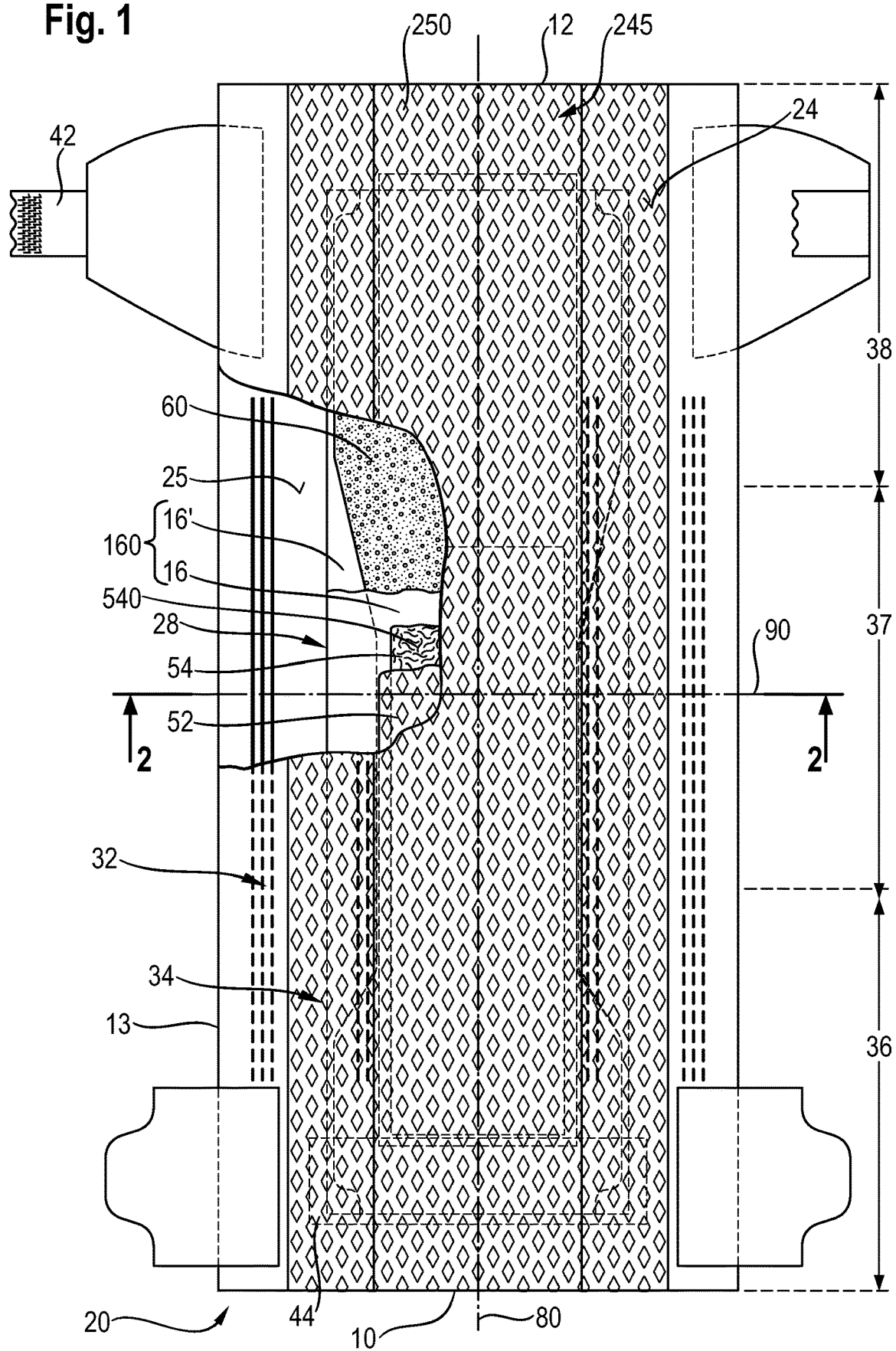
FIG. 1 is an absorbent article in the form of a diaper comprising an exemplary topsheet/acquisition layer laminate wherein the length of the acquisition layer is less that the length of the topsheet according to the present invention with some layers partially removed.

The term "absorbent article" as used herein refers to disposable products such as diapers, pants or feminine hygiene sanitary napkins and the like which are placed against or in proximity to the body of the wearer to absorb and contain the various liquid bodily exudates discharged from the body. Typically these absorbent articles comprise a topsheet, backsheet, an absorbent core and optionally an acquisition layer and/or distribution layer and other components, with the absorbent core normally placed between the backsheet and the acquisition system or topsheet. The absorbent article of the present invention may be a diaper or pant.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

The term "pant" as used herein refers to an absorbent article having fixed edges, a waist opening and leg openings designed for infant or adult wearers. A pant is placed in position on the wearer by inserting the wearer's legs into the leg openings and sliding the pant-type absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened).

The term "extensible" as used herein refers to a material, which, upon application of a force, is capable of undergoing an apparent elongation of equal to or greater than at least 100% of its original length in the machine and/or cross-machine directions at or before reaching the breaking force if subjected to the following test:

The MD and CD tensile properties are measured using a method using WSP 110.4 (05) Option B, with a 50 mm sample width, 60 mm gauge length, and 60 mm/min rate of extension.

It may be desirable that a material is capable of undergoing an apparent elongation of equal to or greater than at least 100% or 110% or 120% or 130% up to 200% in the machine and/or cross-machine directions at or before reaching the breaking force according to the Test Method as set out above.

If a material is capable of undergoing an apparent elongation of less than 100% of its original length if subjected to the above described test, it is "non-extensible" as used herein.

The term "topsheet/acquisition layer laminate web" as used herein refers to an intimate combination of a topsheet web with an acquisition layer, both disposed in a face to face relationship. The topsheet web has a first and second surface. The first surface of the topsheet web is facing towards the body of the wearer when the absorbent article is in use. The acquisition layer is facing the backsheet web. The topsheet web and the acquisition layer have undergone a simultaneous and joint mechanical deformation while the topsheet web and the acquisition layer are combined with each other. The topsheet/acquisition layer laminate web comprises deformations forming three-dimensional protrusions. The topsheet/acquisition layer laminate web is formed by nesting together the topsheet web and acquisition layer such that a majority of the three-dimensional protrusions formed in the topsheet web coincide with and fit together with a majority of the three-dimensional protrusions formed in the acquisition layer, as shown in FIGS. 19A and 20A.

In the topsheet/acquisition layer laminate web, the topsheet web and acquisition layer may be in an intimate contact with each other.

There is no interpenetration of one of the topsheet web or acquisition layer through the respective other topsheet web or acquisition layer in the area of the three-dimensional protrusions of the topsheet/acquisition layer laminate web. The topsheet web and acquisition layer are both extensible such that the topsheet web and/or acquisition layer are able to stretch and do not interpenetrate through the respective ruptured topsheet web or acquisition layer.

In the area of the three-dimensional protrusions, the topsheet web and/or acquisition layer may comprise one or more interruptions. The formation of the one or more interruptions may be due to the properties of the topsheet web and acquisition layer, i.e. apparent elongation of the fibers, fiber mobility, ability to deform and stretch in the area where the three-dimensional protrusions of the topsheet/acquisition layer laminate web are formed. In other words, the topsheet web may be less extensible than the acquisition layer or vice versa, however, the non-ruptured topsheet web or acquisition layer does not interpenetrate the respective ruptured topsheet web or acquisition layer.

Hence, the topsheet/acquisition layer laminate web may be formed by interrupting one of the topsheet web or acquisition layer in the area of the three-dimensional protrusions of the topsheet/acquisition layer laminate web such that the three-dimensional protrusions of the respective other non-interrupted topsheet web or acquisition layer at least partially fit together with the three-dimensional protrusions of the interrupted topsheet web or acquisition layer, as shown in FIGS. 19D, 19E, 20B and 20C.

Alternatively or in addition to what has been set out above, the topsheet/acquisition layer laminate web may be formed by interrupting the topsheet web and acquisition layer in the area of the three-dimensional protrusions of the topsheet/acquisition layer laminate web and the three-dimensional protrusions of the topsheet web coincide with and fit together with the three-dimensional protrusions of the acquisition layer. If the topsheet web and acquisition layer comprise interruptions in the area of the three-dimensional protrusions, the interruptions in the topsheet web in the area of the three-dimensional protrusions of the topsheet/acquisition layer laminate web will not coincide with the interruptions in the acquisition layer in the area of the three-dimensional protrusions of the topsheet/acquisition layer laminate web, as shown in FIGS. 19F and 20D. There is no interpenetration of one of the topsheet web or acquisition layer through the respective other topsheet web or acquisition layer in the area of the three-dimensional protrusions of the topsheet/acquisition layer laminate web.

The term "interruptions", as used herein, refers to holes formed in the topsheet web and/or acquisition layer during the formation of the topsheet/acquisition layer laminate web, and does not include the pores and interstices between fibers typically present in nonwovens.

The term "mechanically deforming and combining" as used herein means that the topsheet web and acquisition layer are put in a face to face relationship and are simultaneously mechanically deformed between a first and second roll and intimately combined at the same time. The mechanical deformation of the topsheet web and acquisition layer depends on the process, the required apparatus but also on the properties of the topsheet web and acquisition layer, i.e. apparent elongation of the fibers, fiber mobility, ability to deform and stretch in the area where the three-dimensional protrusions of the topsheet/acquisition layer laminate web are formed, ability to undergo plastic deformation which sets after existing the first and second roll, or springing partially back due to elastic recovery.

The mechanical deformation may comprise intermeshing the topsheet web together with the acquisition layer between a first and second intermeshing roll. The first intermeshing roll comprises a plurality of ridges and corresponding grooves. The second intermeshing roll comprises a plurality of rows of circumferentially-spaced teeth and corresponding grooves such that a plurality of deformations comprising three-dimensional protrusions is obtained. A tunnel-shaped loop may be one type of three-dimensional protrusion.

The term "topsheet/acquisition layer laminate" as used herein refers to an intimate combination of a topsheet with an acquisition layer, both disposed in a face to face relationship. The topsheet has a first and second surface. The first surface of the topsheet is facing towards the body of the wearer when the absorbent article is in use. The acquisition layer is facing the backsheet. The topsheet and the acquisition layer have undergone a simultaneous and joint mechanical deformation while the topsheet and the acquisition layer are combined with each other. The topsheet/acquisition layer laminate comprises deformations forming three-dimensional protrusions. The topsheet/acquisition layer laminate is formed by nesting together the topsheet and acquisition layer such that a majority of the three-dimensional protrusions formed in the topsheet coincide with and fit together with a majority of the three-dimensional protrusions formed in the acquisition layer, as shown in FIGS. 19A and 20A.

For each three-dimensional protrusion:
  The topsheet is nested into the acquisition layer or vice versa such that the majority of the three-dimensional protrusions of the topsheet and of the acquisition layer coincide with and fit together, as shown in FIGS. 19A and 20A. There is no interpenetration of one of the topsheet or acquisition layer into or through the respective other topsheet or acquisition layer in the area of the three-dimensional protrusions of the topsheet/acquisition layer laminate.
  In addition to what has been set out above, one of the topsheet or acquisition layer may be interrupted in the area of the three-dimensional protrusions of the topsheet/acquisition layer laminate such that the three-dimensional protrusions made of the respective other non-interrupted topsheet or acquisition layer at least partially fit together with the three-dimensional protrusions of the interrupted topsheet or of the interrupted acquisition layer, as shown in FIGS. 19D, 19E, 20B and 20C. There is no interpenetration of one of the topsheet or acquisition layer through the respective other topsheet or acquisition layer in the area of the three-dimensional protrusions of the topsheet/acquisition layer laminate.
  Alternatively or in addition to what has been set out above, the topsheet and acquisition layer may be interrupted in the area of the three-dimensional protrusions of the topsheet/acquisition layer laminate and the three-dimensional protrusions of the topsheet coincide with and fit together with the three-dimensional protrusions of the acquisition layer. The interruptions in the topsheet in the area of the three-dimensional protrusions of the topsheet/acquisition layer laminate may not coincide with the interruptions in the acquisition layer in the area of the three-dimensional protrusions of the topsheet/acquisition layer laminate, as shown in FIGS. 19F and 20D. There is no interpenetration of one of the topsheet or acquisition layer through the respective other topsheet or acquisition layer in the area of the three-dimensional protrusions of the topsheet/acquisition layer laminate.

The term "tunnel-shaped loop" as used herein means that a three-dimensional protrusion of the topsheet/acquisition layer laminate is defined by a plurality of loops extending from the topsheet to the acquisition layer or from the acquisition layer to the topsheet. The plurality of loops comprises one or more fibers made of the topsheet/acquisition layer laminate. The fibers of the plurality of loops are generally aligned with one another such that the plurality of loops form a tunnel-shaped loop. A tunnel-shaped loop may be defined as a cylindania, i.e. a cylinder cut in half along its length, comprising openings at each extremity of the tunnel-shaped loop and a base opening.

The term "a majority of the three-dimensional protrusions" as used herein means that more than 50% or more than 60% or more than 70% or more than 80% or more than 90% or more than 95% or more than 98% of the three-dimensional protrusions in the topsheet/acquisition layer laminate web or in the topsheet/acquisition layer laminate of the absorbent article, each comprises a base forming an opening, an opposed distal portion and the one or more side wall between the base and the distal portion of the three-dimensional protrusion. The base, distal portion and one or more side wall are formed by fibers such that the three-dimensional protrusion has only an opening at the base (as exemplary shown in a FIG. 19A).

The term "machine direction" or "MD" as used herein means the path that material, such as a web, follows through a manufacturing process.

The term "cross-machine direction" or "CD" as used herein means the path that is perpendicular to the machine direction in the plane of the web.

The term "cellulosic fiber" as used herein refers to natural fibers which typically are wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web.

The term "dry-laid fiber" as used herein means fibers which have been provided in a fluid medium which is gaseous (air).

The term "wet-laid fiber" as used herein comprises cellulosic fibers which have been suspended in an aqueous medium, such as water, before being converted into a web and dried according to a wet-laid papermaking process.

The term "web" as used herein means a material capable of being wound into a roll. Webs may be nonwovens.

The term "nonwoven web" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

The term "absorbent core" as used herein refers to a component, which is placed or is intended to be placed within an absorbent article and which comprises an absorbent material enclosed in a core wrap. The term "absorbent core" does not include an acquisition or distribution layer or any other component of an absorbent article which is not either an integral part of the core wrap or placed within the core wrap. The absorbent core is typically the component of an absorbent article which comprises all, or at least the majority of, superabsorbent polymer and has the highest absorbent capacity of all the components of the absorbent article.

The term "substantially free of absorbent material" or "substantially absorbent material free" as used herein means that the basis weight of the absorbent material in the substantially absorbent material free areas is at least less than 10%, in particular less than 5%, or less than 2%, of the basis weight of the absorbent material in the rest of the absorbent core.

The term "superabsorbent polymers" (herein abbreviated as "SAP") as used herein refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 25 g/g, or from 20 to 50 g/g, or from 20 to 40 g/g, or 25 to 35 g/g. The SAP useful in the invention includes a variety of water-insoluble, but water-swellable polymers capable of absorbing large quantities of liquid bodily exudates.

The term "joined to" as used herein encompasses configurations in which an element is directly secured to another element by affixing the element directly to the other element; and configurations in which the element is indirectly secured to the other element by affixing the element to intermediate member(s) which in turn are affixed to the other element. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement.

The term "joined adjacent to the transversal edges" as used herein means that when a first and/or second transversal edge of a first layer is/are joined adjacent to a first and/or second transversal edges of a second layer, the first and/or second transversal edge of the first layer are disposed within an area spaced inboard from the first and/or second transversal edge of the second layer. The area has a width which is from 1 to 30% of the width of the second layer.

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essential of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "advantageously" and the likes also qualify features which are not intended to limit the scope of the claims unless specifically indicated to do so.

General Description of the Absorbent Article 20

Figure 4:
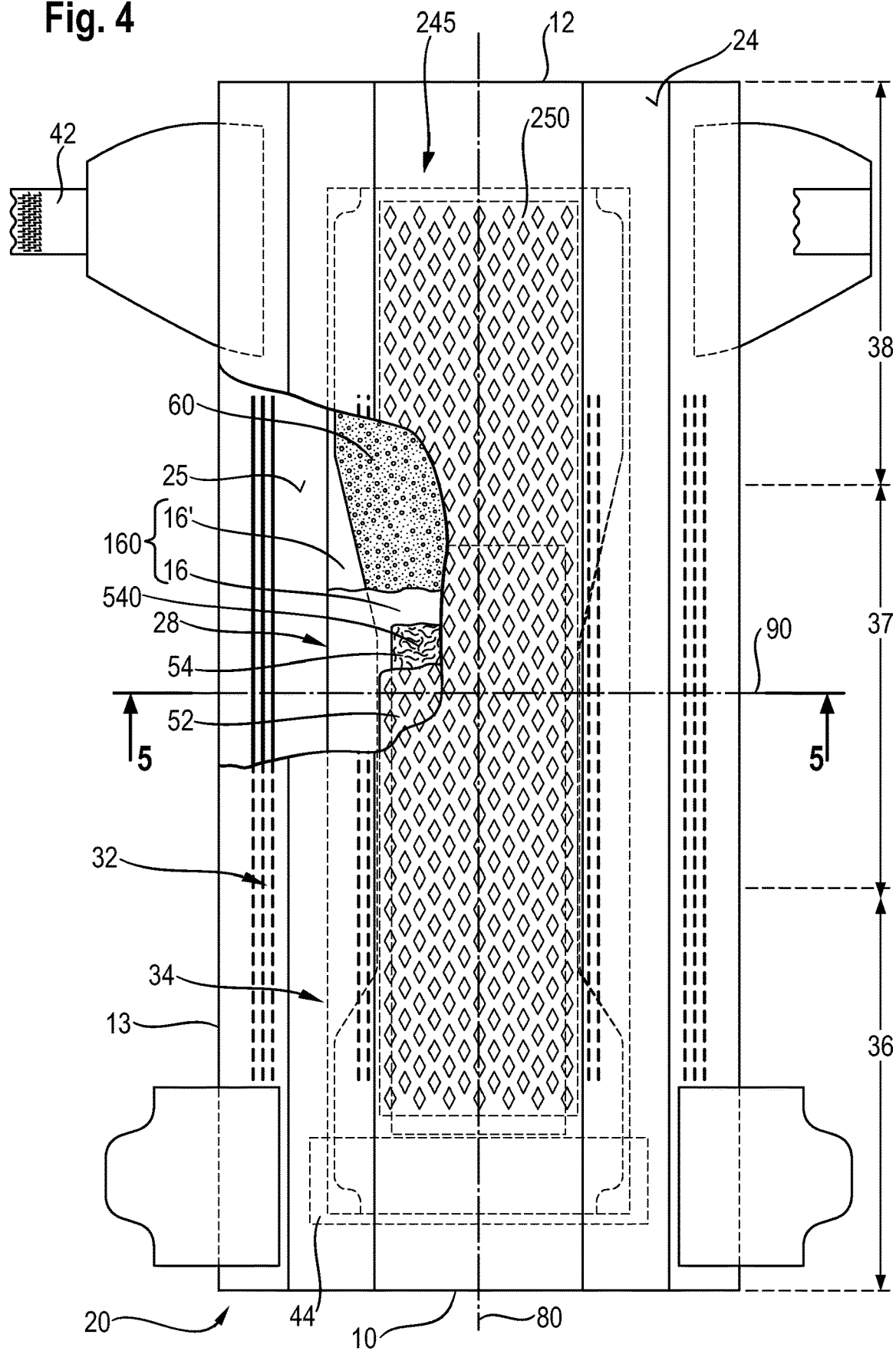
FIG. 4 is an absorbent article in the form of a diaper comprising an exemplary topsheet/acquisition layer laminate wherein the three-dimensional protrusions of the topsheet/acquisition layer laminate are only formed where the topsheet overlaps the acquisition layer in the topsheet/acquisition layer laminate, according to the present invention with some layers partially removed.
Figure 5:
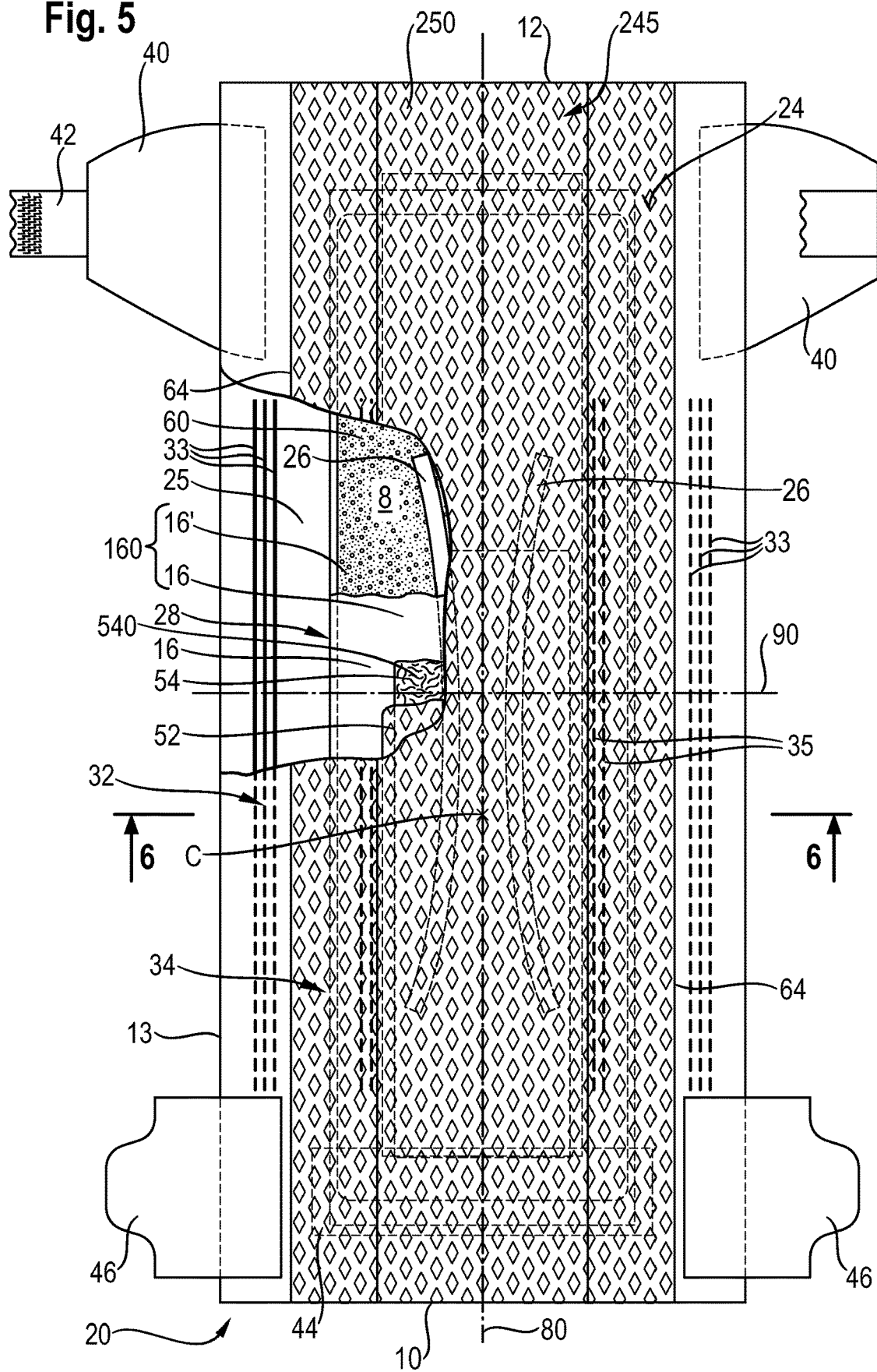
FIG. 5 is an absorbent article in the form of a diaper comprising an exemplary topsheet/acquisition layer with another type of absorbent core according to the present invention with some layers partially removed.

An exemplary absorbent article 20 in which the absorbent core 28 of the invention can be used is a taped diaper 20 as represented in FIG. 1; FIG. 4 and FIG. 5 with a different absorbent core construction. FIG. 1; FIG. 4 and FIG. 5 are top plan views of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles.

The absorbent article 20 comprises a topsheet/acquisition layer laminate 245 formed from a liquid permeable topsheet 24 and an acquisition layer 52. In other words, the absorbent article 20 comprises a liquid permeable topsheet 24 and an acquisition layer 52 characterized in that the topsheet 24 and the acquisition layer 52 are joined to form a topsheet/acquisition layer laminate 245. The absorbent article 20 comprises a liquid impermeable backsheet 25 and an absorbent core 28 between the topsheet 24 and the backsheet 25. The absorbent article 20 comprises a front edge 10, a back edge 12, and two longitudinal side edges 13. The front edge 10 is the edge of the absorbent article 20 which is intended to be placed towards the front of the user when worn, and the back edge 12 is the opposite edge. The absorbent article 20 may be notionally divided by a longitudinal axis 80 extending from the front edge 10 to the back edge 12 of the absorbent article 20 and dividing the absorbent article 20 in two substantially symmetrical halves relative to this axis, when viewing the absorbent article 20 from the wearer facing side in a flat out configuration, as exemplarily shown in FIG. 1, FIG. 4 and FIG. 5.

The absorbent article 20 may comprise a distribution layer 54 which may comprise a dry-laid fibrous structure or a wet-laid fibrous structure. The topsheet/acquisition layer laminate 245 is facing towards the body of the wearer when the absorbent article 20 is in use.

The wet-laid fibrous structure comprising wet-laid fibers may have a Wet burst Strength from 50 to 500 g according to the Wet Burst Strength Test Method and combinations thereof.

The distribution layer 54 may comprise a dry-laid fibrous structure. The dry-laid fibrous structure may comprise dry-laid fibers 540. The dry-laid fibrous structure may comprise a mixture including superabsorbent polymers and dry-laid fibers. The dry-laid fibers may comprise intra-fiber cross-linked cellulosic fibers.

The distribution layer 54 may be free of tow fibers.

The distribution layer 54 may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf).

Exemplary chemically cross-linked cellulosic fibers suitable for a distribution layer 54 are disclosed in U.S. Pat. Nos. 5,549,791; 5,137,537; WO95/34329 or US2007/118087. Exemplary cross-linking agents may include polycarboxylic acids such as citric acid and/or polyacrylic acids such as acrylic acid and maleic acid copolymers.

The distribution layer may typically have an average basis weight of from 30 to 400 g/m$^2$, in particular from 100 to 300 g/m$^2$. The density of the distribution layer may vary depending on the compression of the article, but may be of between 0.03 to 0.15 g/cm$^3$, in particular 0.08 to 0.10 g/cm$^3$ measured at 0.30 psi (2.07 kPa).

The distribution layer 54 may have an average basis weight of from 30 to 400 gsm, in particular from 100 to 300 gsm or from 50 to 250 gsm.

As explained more in a process detailed below, a topsheet web 240 and an acquisition layer 52 are simultaneously mechanically deformed and combined together to form a topsheet/acquisition layer laminate web 2450. The topsheet/acquisition layer laminate web 2450 forms the topsheet/acquisition layer laminate 245 in the absorbent article 20. The topsheet/acquisition layer laminate 245 comprises mechanical deformations forming three-dimensional protrusions 250. The mechanical deformations provide a three-dimensional structure to the topsheet/acquisition layer laminate 245.

The absorbent article 20 may comprise elasticized gasketing cuffs 32 present between the topsheet 24 and the backsheet 25 and upstanding barrier leg cuffs 34. FIGS. 1, 4 and 5 also show other typical diaper components such as a fastening system comprising fastening tabs 42 attached towards the back edge 12 of the absorbent article 20 and cooperating with a landing zone 44 towards the front edge 10 of the absorbent article 20. The absorbent article 20 may also comprise other typical components, which are not represented in the Figures, such as a back elastic waist feature, a front elastic waist feature, transverse barrier cuff(s), a lotion application, etc.

Figure 7:
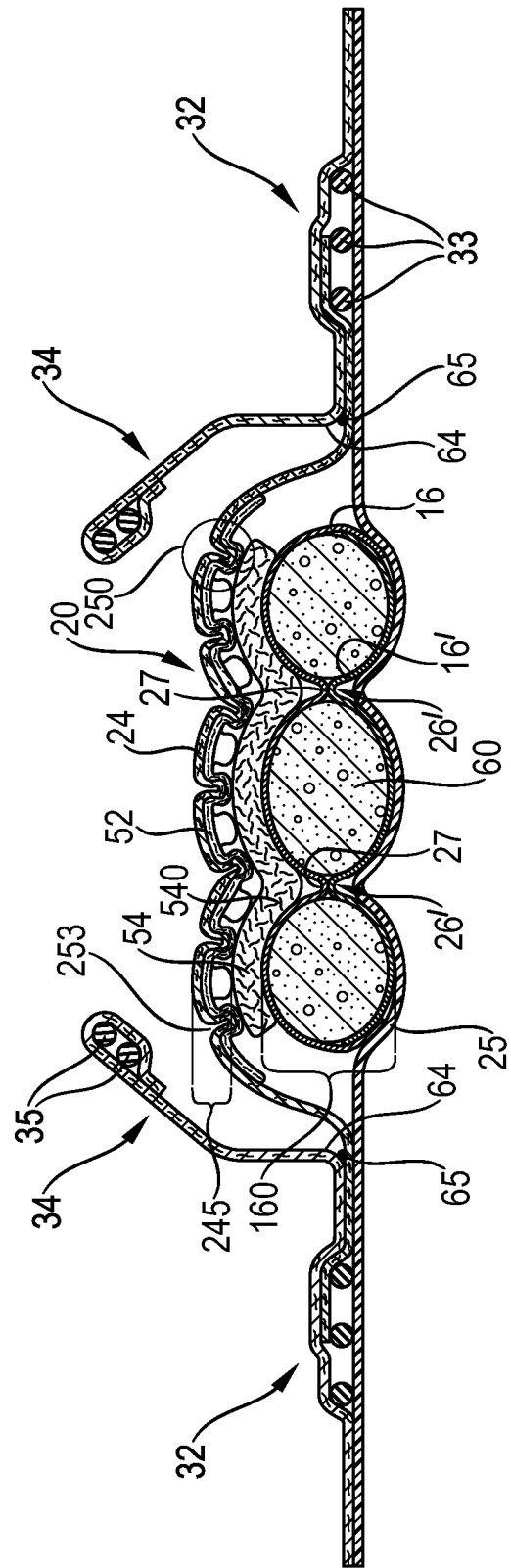
FIG. 7 is a transversal cross-section of the absorbent article of FIG. 5 taken at the same point as FIG. 6 where channels have formed as a result the absorbent article being loaded with liquid bodily exudates.

As shown in FIG. 7, the barrier leg cuffs 34 may be delimited by a proximal edge 64 joined to the rest of the article 20, typically the topsheet 24 and/or the backsheet 25, and a free terminal edge intended to contact and form a seal with the wearer's skin. The barrier leg cuffs 34 may be joined at the proximal edge 64 by a bond 65 which may be made for example by adhesive bonding, fusion bonding or combination of known bonding means. Each barrier leg cuff 34 may comprise one, two or more elastic strings 35 to provide a better seal. The gasketing cuffs 32 may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 for example between the topsheet 24 and the backsheet 25 in the area of leg openings.

The absorbent article 20 can also be notionally divided by a transversal axis 90 in a front region and a back region of equal length measured on the longitudinal axis, when the absorbent article 20 is in a flat state. The absorbent article's transversal axis 90 is perpendicular to the longitudinal axis 80 and placed at half the length of the absorbent article 20. The length of the absorbent article 20 can be measured along the longitudinal axis 80 from the front edge 10 to the back edge 12 of the absorbent article 20. The topsheet 24, acquisition layer 52, distribution layer 54 and absorbent core 28 each have a width which can be measured from their respective transversal edges and in parallel to the transversal axis 90.

The absorbent article 20 is notionally divided in a front region 36, a back region 38 and a crotch region 37 located between the front and the back region of the absorbent article 20. Each of the front, back and crotch region is ⅓ of the length of the absorbent article 20. The absorbent article may also comprise front ears 46 and back ears 40 as it is known in the art.

The absorbent core 28 of the present invention may comprise as absorbent material 60 a blend of cellulosic fibers (so called "airfelt") and superabsorbent polymers in particulate form encapsulated in one or more substrates, see for example U.S. Pat. No. 5,151,092 (Buell). Alternatively, the absorbent core 28 may be airfelt free as described in detail below.

Generally, the absorbent core 28 can be defined by the periphery of the layer formed by the absorbent material 60 within the core wrap 160, as seen from the top side of the absorbent core 28. The absorbent core 28 can take various shapes, in particular display a so-called "dog bone" or "hour-glass" shape, which shows a tapering along its width towards the middle or "crotch" region of the core. In this way, the absorbent core 28 may have a relatively narrow width in an area of the absorbent core 28 intended to be placed in the crotch region of the absorbent article. This may provide for example better wearing comfort. The absorbent core 28 may thus have a width (as measured in the transversal direction) at its narrowest point which is less than about 100 mm, 90 mm, 80 mm, 70 mm, 60 mm or even less than about 50 mm. The absorbent core 28 can also be generally rectangular, see for example as shown in FIG. 5, but other deposition areas can also be used such as a "T" or "Y" or "hour-glass" or "dog-bone" shape (See for example FIG. 4).

Some components of the absorbent article 20 will now be discussed in more details.

"Airfelt-Free" Absorbent Core 28

The absorbent core 28 of the invention may comprise an absorbent material 60 enclosed within a core wrap 160. The absorbent material 60 may comprise from 80% to 100% of SAP, such as SAP particles, by total weight of the absorbent material 60. The core wrap 160 is not considered as an absorbent material 60 for the purpose of assessing the percentage of SAP in the absorbent core 28.

Figure 2:
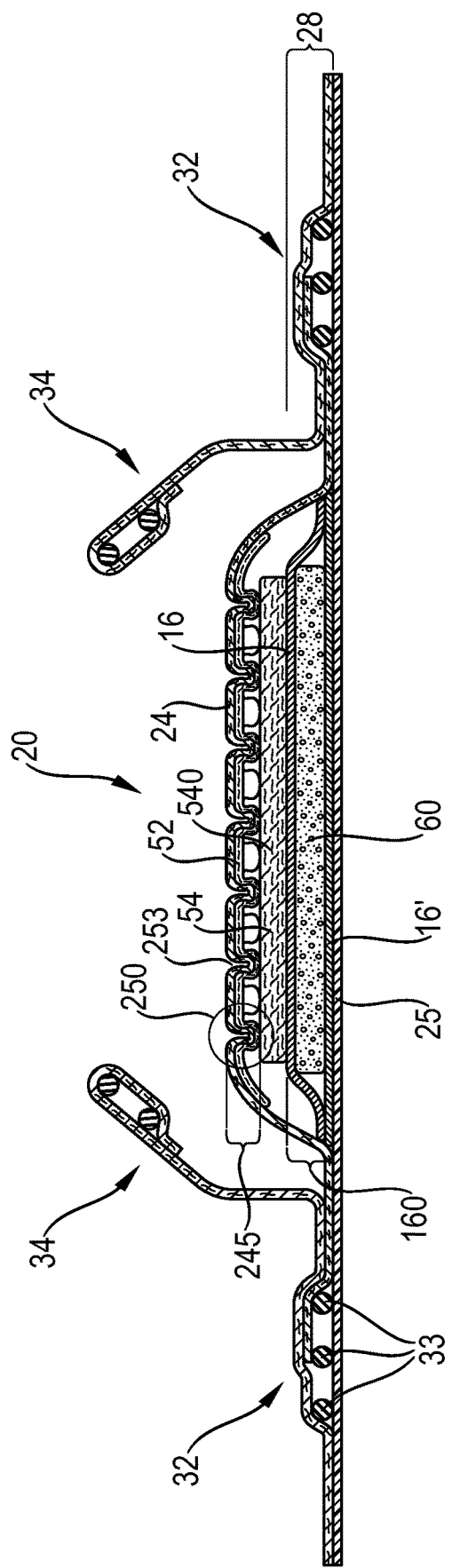
FIG. 2 is a transversal cross-section of the diaper of FIG. 1.
Figure 3:
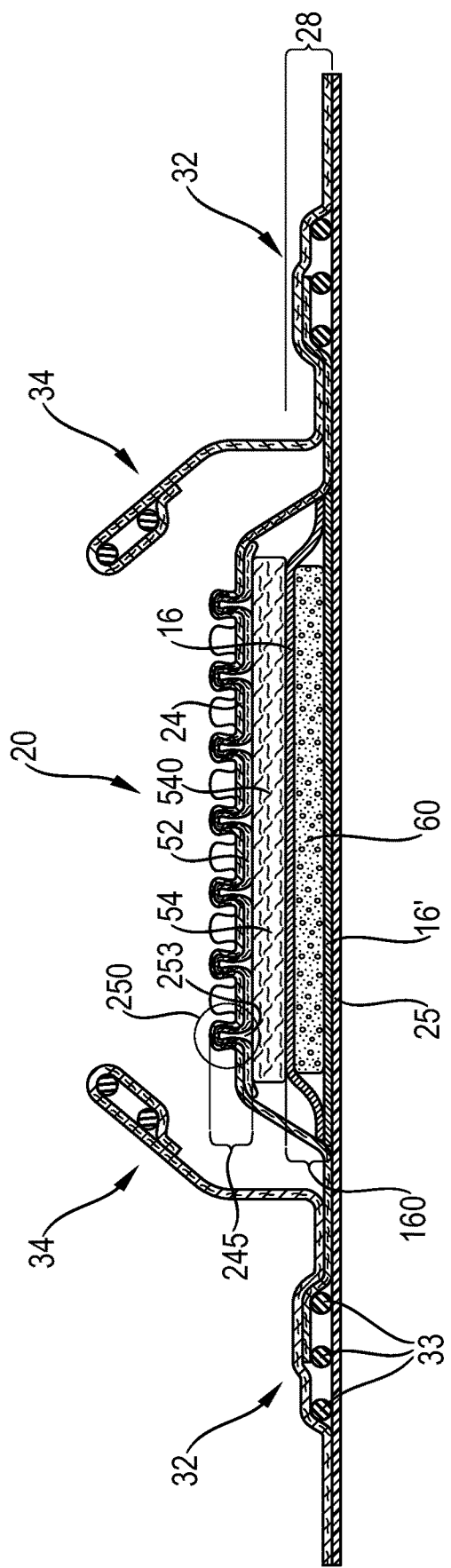
FIG. 3 is a transversal cross-section of the diaper of FIG. 1.

By "absorbent material" it is meant a material which has at least some absorbency and/or liquid retaining properties, such as SAP, cellulosic fibers as well as some hydrophilically treated synthetic fibers. Typically, adhesives used in making absorbent cores have no absorbency properties and are not considered as absorbent material. The SAP content may be substantially higher than 80%, for example at least 85%, at least 90%, at least 95% and even up to and including 100% of the weight of the absorbent material 60 contained within the core wrap 160. This above SAP content substantially higher than 80% SAP may provide a relatively thin absorbent core 28 compared to conventional absorbent cores typically comprising between 40-60% SAP and 40-60% of cellulosic fibers. The absorbent material 60 of the invention may in particular comprise less than 10% weight percent, or less than 5% weight percent, or even be substantially free of natural and/or synthetic fibers. The absorbent material 60 may advantageously comprise little or no cellulosic fibers, in particular the absorbent core 28 may comprise less than 15%, 10%, or 5% (airfelt) cellulosic fibers by weight of the absorbent core 28, or even be substantially free of cellulose fibers. Such absorbent core 28 may be relatively thin and thinner than conventional airfelt cores. FIG. 1, FIG. 2 and FIG. 3 are illustrations of an absorbent article 20 comprising an "airfelt-free" absorbent core 28.

"Airfelt-free" absorbent cores 28 comprising relatively high amount of SAP with various absorbent core designs have been proposed in the past, see for example in U.S. Pat. No. 5,599,335 (Goldman), EP1447066A1 (Busam), WO95/11652 (Tanzer), US2008/0312622A1 (Hundorf), and WO2012/052172 (Van Malderen).

The absorbent core 28 of the invention may comprise adhesive for example to help immobilizing the SAP within the core wrap 160 and/or to ensure integrity of the core wrap 160 in particular when the core wrap 160 is made of one or more substrates. The core wrap 160 will typically extend over a larger area than strictly needed for containing the absorbent material 60 within.

Core Wrap

The absorbent material 60 is encapsulated in one or more substrates. The core wrap 160 comprises a top side 16 facing the topsheet 24 and a bottom side 16' facing the backsheet 25. The core wrap 160 may be made of a single substrate folded around the absorbent material 60. The core wrap 160 may be made of two substrates (one mainly providing the top side 16 and the other mainly providing the bottom side 16') which are attached to another, as exemplarily shown in FIG. 2. Typical configurations are the so-called C-wrap and/or sandwich wrap. In a C-wrap, as exemplarily shown in FIG. 6, the longitudinal and/or transversal edges of one of the substrate are folded over the other substrate to form flaps. These flaps are then bonded to the external surface of the other substrate, typically by bonding with an adhesive. The so called C-wrap construction can provide benefits such as improved resistance to bursting in a wet loaded state compared to a sandwich seal.

The core wrap 160 may be formed by any materials suitable for receiving and containing the absorbent material 60. The core wrap 160 may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as polyethylene (PE), polyethylene terephthalate (PET) and in particular polypropylene (PP).

"Airfelt-Free" Absorbent Core 28 Comprising Substantially Absorbent Material Free Areas 26

The absorbent core 28 may comprise an absorbent material deposition area 8 defined by the periphery of the layer formed by the absorbent material 60 within the core wrap 160.

Figure 6:
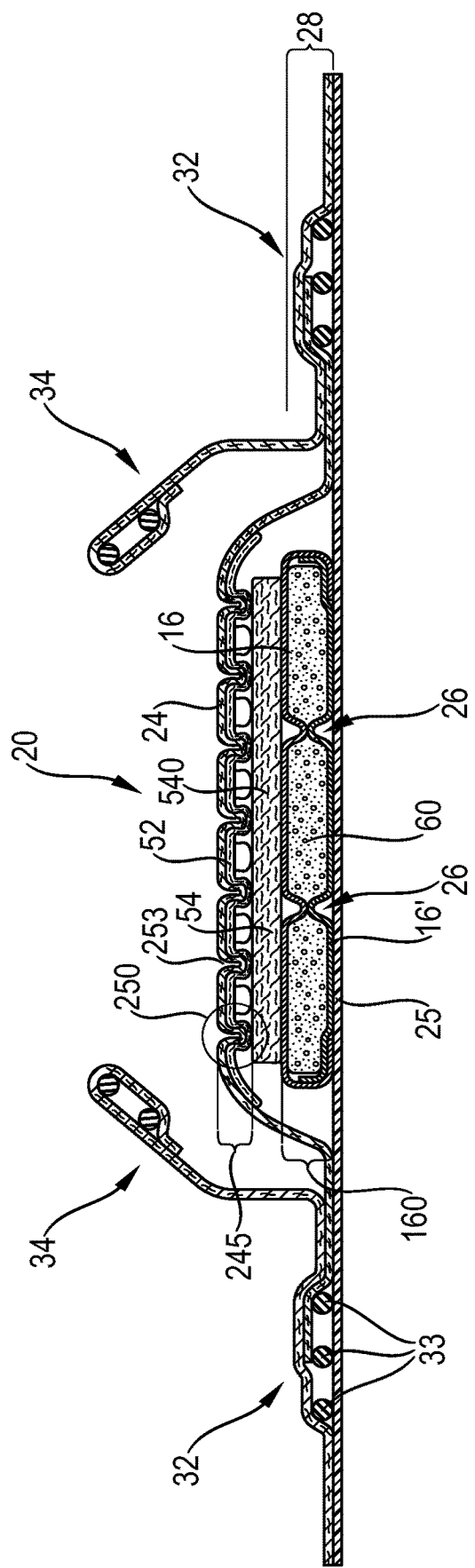
FIG. 6 is a transversal cross-section of a diaper of FIG. 5.

The absorbent core 28 may comprise one or more substantially absorbent material free area(s) 26 which is/are substantially free of absorbent material 60 and through which a portion of the top side 16 of the core wrap 160 is attached by one or more core wrap bond(s) 27 to a portion of the bottom side 16' of the core wrap 160, as shown in FIGS. 5 and 6. In particular, there can be no absorbent material 60 in these areas. Minimal amount such as contaminations with absorbent material 60 that may occur during the making process are not considered as absorbent material 60. The one or more substantially absorbent material free area(s) 26 may be advantageously confined by the absorbent material 60, which means that the substantially absorbent material free area(s) 26 do(es) not extend to any of the edge of the absorbent material deposition area 8.

If the substantially absorbent material free area 26 extends to any of the edges of the absorbent material deposition area 8, each substantially absorbent material free area 26 may have areas of absorbent material 60 on either side of each substantially absorbent material free area 26.

The absorbent core 28 may comprise at least two substantially absorbent material free areas 26 symmetrically disposed on both sides of the longitudinal axis of the absorbent core 28, as shown in FIG. 5.

The substantially absorbent material free area(s) 26 may be straight and completely oriented longitudinally and parallel to the longitudinal axis but also may be curved or have one or more curved portions.

Furthermore, in order to reduce the risk of liquid bodily exudate leakages, the substantially absorbent material free area(s) 26 advantageously do not extend up to any of the edges of the absorbent material deposition area 8, and are therefore surrounded by and fully encompassed within the absorbent material deposition area 8 of the absorbent core 28. Typically, the smallest distance between a substantially absorbent material free area 26 and the closest edge of the absorbent material deposition area 8 is at least 5 mm.

"Airfelt free" absorbent cores 28 comprising substantially absorbent material free areas 26 have been proposed, see for example in EP Patent Application No. 12196341.7.

One or more channel(s) 26' along the substantially absorbent material free area(s) 26 in the absorbent core 28 may start forming when the absorbent material 60 absorbs a liquid and starts swelling. As the absorbent core 28 absorbs more liquid, the depressions within the absorbent core 28 formed by the channel(s) 26' will become deeper and more apparent to the eye and the touch. The formation of the channel(s) 26' may also serve to indicate that the absorbent article 20 has been loaded with liquid bodily exudates. The core wrap bond(s) 27 should remain substantially intact at least during a first phase as the absorbent material 60 absorbs a moderate quantity of liquid bodily exudates.

As shown in FIG. 7, when the absorbent material swells, the core wrap bonds 27 remain at least initially attached in the substantially absorbent material free areas 26. The absorbent material 60 swells in the rest of the absorbent core 28 when it absorbs a liquid, so that the core wrap 160 thus forms channels 26' along the substantially absorbent material free areas 26 comprising the core wrap bonds 27.

The Process of Making the Absorbent Article Having a Topsheet/Acquisition Layer Laminate Web A topsheet/acquisition layer laminate 245 having a three-dimensional structure is provided.

A process 100 of making an absorbent article 20 comprises the step of providing a liquid permeable topsheet web 240 extending substantially continuously in a machine direction, the topsheet web 24 having a first and second surface, a liquid impermeable backsheet web 2555 extending substantially continuously in the machine direction, and an acquisition layer 52 having a first and second surface. The first surface of the topsheet web 24 will be facing towards the body of the wearer when the absorbent article 20 is in use. The topsheet web 240, and thus the topsheet 24, and the acquisition layer 52 comprise fibers.

The topsheet web 240 and acquisition layer 52 are aligned in a face to face relationship such that the second surface of the topsheet web 240 is in contact with the first surface of the acquisition layer 52. The topsheet web 240 and the acquisition layer 52 are simultaneously mechanically deformed and combined together. The topsheet web 240 and acquisition layer 52 are nested together such that the majority of the three-dimensional protrusions formed in the topsheet web 240 coincide with and fit together with the majority of the three-dimensional protrusions formed in the acquisition layer 52 to provide a topsheet/acquisition layer laminate web 2450 having three-dimensional protrusions 250. This means that both topsheet web 240 and acquisition layer 52 are mechanically deformed and combined together at the same time. The topsheet/acquisition layer laminate web 2450 has a first surface comprising the second surface of the acquisition layer 52.

A portion of the backsheet web 2555 is joined to a portion of the topsheet web 240 of the topsheet/acquisition layer laminate web 2450 such that the first surface of the topsheet/acquisition layer laminate web 2450 is facing towards the backsheet web 2555.

Figure 8:
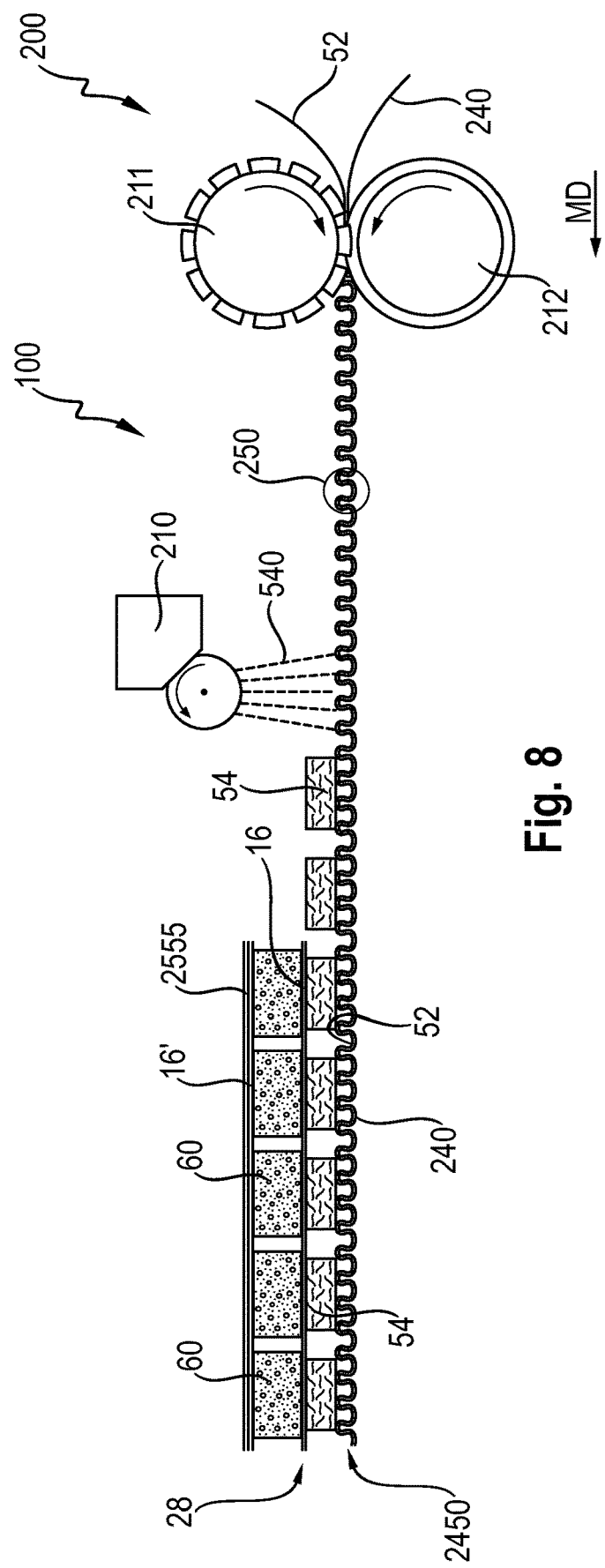
FIG. 8 is a side schematic view of an example of a process according to the present invention.

The process 100 of making an absorbent article 20 may comprise the step of providing a dry-laid fibrous structure or a wet-laid fibrous, as shown in FIG. 8.

As shown in FIG. 8, the topsheet web 240 and acquisition layer 52 are mechanically deformed and combined between a first and second roll (211, 212) to form a topsheet/acquisition layer laminate web 2450. Dry-laid fibers 540 of the dry-laid fibrous structure (as shown in FIG. 8, provided from a distribution material feeder 210) or wet-laid fibrous structure may be deposited on the first surface of the topsheet/acquisition layer laminate web 2450 or the backsheet web 2555.

A portion of the backsheet web 2555 may be joined to a portion of the topsheet web 240 of the topsheet/acquisition layer laminate web 2450 such that the dry-laid fibrous structure or the wet-laid fibrous structure are between the topsheet/acquisition layer laminate web 2450 and the backsheet web 2555.

The dry-laid fibrous structure may comprise dry-laid fibers 540. The dry-laid fibrous structure may comprise a mixture including superabsorbent polymers (SAP) and dry-laid fibers. The dry-laid fibers may comprise intra-fiber cross-linked cellulosic fibers.

The process may further comprise the step of providing an absorbent core 28 which comprises an absorbent material 60. The absorbent material 60 may comprise from 80% to 100% of SAP, such as SAP particles, by total weight of the absorbent material 60.

Another type of absorbent material may be water-absorbing foams based on cross-linked monomers comprising acid groups, see for example from EP 0 858 478 B1, WO 97/31971 A1, WO 99/44648 A1 and WO 00/52087 A1.

Hence, the first surface of the topsheet/acquisition layer laminate 245 can carry the material of the distribution layer 54 or the absorbent material 60 of the absorbent core 28.

A majority of the three-dimensional protrusions 250 may be more than 50% or more than 60% or more than 70% or more than 80% or more than 90% or more than 95% or more than 98% of the three-dimensional protrusions 250 in the topsheet/acquisition layer laminate web 2450 or in the topsheet/acquisition layer laminate 245.

The absorbent article 20 may comprise gasketing cuffs 32. The majority of the three-dimensional protrusions 250 of the topsheet/acquisition layer laminate 245 may at least be present in the area where the topsheet 24 overlaps the acquisition layer 52 in the topsheet/acquisition layer laminate 245. However, the majority of the three-dimensional protrusions 250 of the topsheet/acquisition layer laminate 245 may also be present in the acquisition layer 52 and in the topsheet 24, in the area which extends parallel to the transversal axis 90 of the absorbent article 20. The majority of the three-dimensional protrusions 250 of the topsheet/acquisition layer laminate 245 may be present in the area which extends parallel to the longitudinal axis 80 of the absorbent article 20, but which does not extend beyond the area where gasketing cuffs 32 is attached to the absorbent article 20, in particular to the topsheet 24, as shown in FIG. 1. In that case, the majority of the three-dimensional protrusions 250 which are formed in the topsheet 24 of the topsheet/acquisition layer laminate 245, are formed from the fibers of the topsheet 24.

Alternatively, the majority of the three-dimensional protrusions of the topsheet/acquisition layer laminate 245 may be present in the area which extends parallel to the transversal axis 90 of the absorbent article 20 such that the area comprising the three-dimensional protrusions of the topsheet 24 overlaps the acquisition layer 52. The length of the area of the majority of the three-dimensional protrusions of the topsheet/acquisition layer laminate 245 may be from 5% to 60% or from 10% to 40% wider than the length of the acquisition layer 52 of the topsheet/acquisition layer laminate 245. The majority of the three-dimensional protrusions of the topsheet/acquisition layer laminate 245 may be present in the area which extends parallel to the longitudinal axis 80 of the absorbent article 20 such that the area comprising the majority of the three-dimensional protrusions of the topsheet 24 overlaps the acquisition layer 52. The width of the area of the majority of the three-dimensional protrusions of the topsheet/acquisition layer laminate 245 may be from 5% to 60% or from 10% to 40% wider than the width of the acquisition layer 52 of the topsheet/acquisition layer laminate 245. In that case, the majority of the three-dimensional protrusions 250 which are formed in the topsheet 24 of the topsheet/acquisition layer laminate 245, are formed from the fibers of the topsheet 24.

In still another alternative, the majority of the three-dimensional protrusions 250 of the topsheet/acquisition layer laminate 245 may only be present where the topsheet 24 overlaps the acquisition layer 52 in the topsheet/acquisition layer laminate 245, as shown in FIG. 4.

Hence, the majority of the three-dimensional protrusions 250 can provide an impression of depth and can support the caregiver's perception that the absorbent article 20 is well able to absorb the liquid bodily exudates.

The majority of the three-dimensional protrusions 250 of the topsheet/acquisition layer laminate 245 can have a measured protrusion height from 0.3 mm to 5 mm or from 0.5 mm to 3 mm or from 1.0 mm to 2.0 mm according to the Protrusion Height Test Method as described below.

The majority of the three-dimensional protrusions 250 of the topsheet/acquisition layer laminate 245 can have a measured protrusion base width of the three-dimensional protrusions 250 from 0.5 mm to 10 mm or from 0.5 mm to 5 mm or from 0.5 mm to 3.0 mm or from 1.0 mm to 2.5 mm or from 1.5 mm to 2.5 mm according to the Protrusion Base Width Test Method as described below.

The majority of the three-dimensional protrusions 250 having a shape with a specific height and width can provide an impression of depth and can support the caregiver's perception that the absorbent article 20 is well able to absorb the liquid bodily exudates.

These three-dimensional protrusions 250 provide void volume to receive the liquid bodily exudates. At the same time, the topsheet 24 and acquisition layer 52 in the topsheet/acquisition layer laminate 245 may be in an intimate contact because the topsheet 24 and acquisition layer 52 are nested together. Also, the topsheet/acquisition layer laminate 245 is in close contact with the underlaying layer, i.e. the distribution layer 54. Hence, the liquid bodily exudates are transmitted more efficiently from the topsheet/acquisition layer laminate 245 to the distribution layer 54, which improves the dryness of the topsheet 24 of the topsheet/acquisition layer laminate 245. Rewet is reduced at the skin of the wearer. The topsheet/acquisition layer laminate 245 may also enable more efficient use of an absorbent core 28. Overall, the topsheet 24 of the topsheet/acquisition layer laminate 245 can have an improved dryness than a three-dimensional topsheet 24 placed on top of an acquisition layer 52.

The majority of the three-dimensional protrusions 250 may comprise void areas 253 which do not contact the skin of the wearer. The absorbent article 20 may be in less contact with the skin of the wearer in comparison with a flat topsheet. The void areas 253 of the topsheet/acquisition layer laminate 245 can help the air to permeate between the skin of the wearer and the topsheet/acquisition layer laminate 245. Hence, the void areas 253 of the topsheet/acquisition layer laminate 245 can improve the breathability of the topsheet/acquisition layer laminate 245.

In addition to improve dryness, the void areas 253 of the topsheet/acquisition layer laminate 245 can also allow feces to be absorbed and acquired within them. In that case, the present invention is suitable to absorb feces of relatively low viscosity.

The topsheet 24 and the acquisition layer 52 in the topsheet/acquisition layer laminate 245 may be in an intimate contact with each other.

A width of the acquisition layer 52 is less than a width of the topsheet 24 in a cross direction. In the absorbent article 20 comprising the longitudinal axis 80 and the transversal axis 90 perpendicular to the longitudinal axis 80, the width of the acquisition layer 52 in a direction parallel to the transversal axis 90 is less than the width of the topsheet 24 in a direction parallel to the transversal axis 90. If the width of both topsheet 24 and acquisition layer 52 were the same, wicking of the liquid bodily exudates underneath the gasketing cuffs 32 might occur. Hence, the liquid bodily exudates might not be properly absorbed by the absorbent core 28, which may lead to leakage of the liquid bodily exudates out of the absorbent article 20. If the width of the acquisition layer 52 is less that the width of the topsheet 24 in a cross direction, the acquisition layer 52 which may receive the liquid bodily exudates from the topsheet 24 can directly transmit the liquid bodily exudates to the distribution layer 54 in order to be subsequently absorb by the absorbent core 28. Hence, the liquid bodily exudates temporary stored in the acquisition layer 52 of the topsheet/acquisition layer laminate 245 will not readily be drawn towards and underneath the gasketing cuffs 32 by capillary forces. Leakage can thus be reduced by having the width of the acquisition layer 52 less that the width of the topsheet 24 in the topsheet/acquisition layer laminate 245 in a direction parallel to the transversal axis 90.

In order to help reducing leakage and rewet, the width of the acquisition layer 52 of the topsheet/acquisition layer laminate 245 may not be more than 40% wider than the width of the distribution layer 54 and/or more than 20% wider than the width of the absorbent core 28 in a direction parallel to the transversal axis 90. In that case, the liquid bodily exudates may not accumulate at or adjacent to the transversal edges of the acquisition layer. Wicking of the liquid bodily exudates underneath the gasketing cuffs 32 is prevented. Indeed, when the acquisition layer 52 of the topsheet/acquisition layer laminate 245 is no more than 20% wider than the width of the absorbent core 28, the liquid bodily exudates can readily be transported into the absorbent core 28, which can efficiently drain the fluid from the acquisition layer 52 into the absorbent core 28. Wicking of the liquid bodily exudates form the acquisition layer 52 underneath the gasketing cuffs 32 is prevented.

The acquisition layer 52 can receive the liquid bodily exudates that pass through the topsheet 24 and can distribute them to underlying absorbent layers. In such a case, the topsheet 24 in the topsheet/acquisition layer laminate 245 may be less hydrophilic than the acquisition layer 52. The topsheet 24 of the topsheet/acquisition layer laminate 245 can be readily dewatered.

In order to enhance dewatering of the topsheet 24 of the topsheet/acquisition layer laminate 245, the pore size of the acquisition layer 52 may be reduced. For this, the acquisition layer 52 may made of fibers with relatively small denier. The acquisition layer 52 may also have an increased density.

The process may comprise the step of joining the portion of the backsheet web 2555 to the portion of the topsheet web 240 at or adjacent to the transversal edges of the first surface of the topsheet/acquisition layer laminate web 2450 in the cross direction. The transversal edges of the first surface of the topsheet/acquisition layer laminate web 2450 do not comprise any acquisition layer 52. When the portion of the backsheet web 2555 is joined to the portion of the topsheet web 240 of the topsheet/acquisition layer laminate web 2450, the acquisition layer 52 is then enveloped between the topsheet web 240 and the backsheet web 2555.

The process may comprise the step of cutting into individual absorbent articles comprising a backsheet 25, a topsheet 24 and an acquisition layer 52, characterized in that the topsheet 24 and acquisition layer 52 are joined to form a topsheet/acquisition layer laminate 245.

The topsheet/acquisition layer laminate web 2450 may be produced at a particular location in the process setup. Hence, the topsheet/acquisition layer laminate web 2450 might be not available to carry the dry-laid fibers 540 of the dry-laid fibrous structure of the distribution layer 54 at the desired location of the process.

Figure 9:
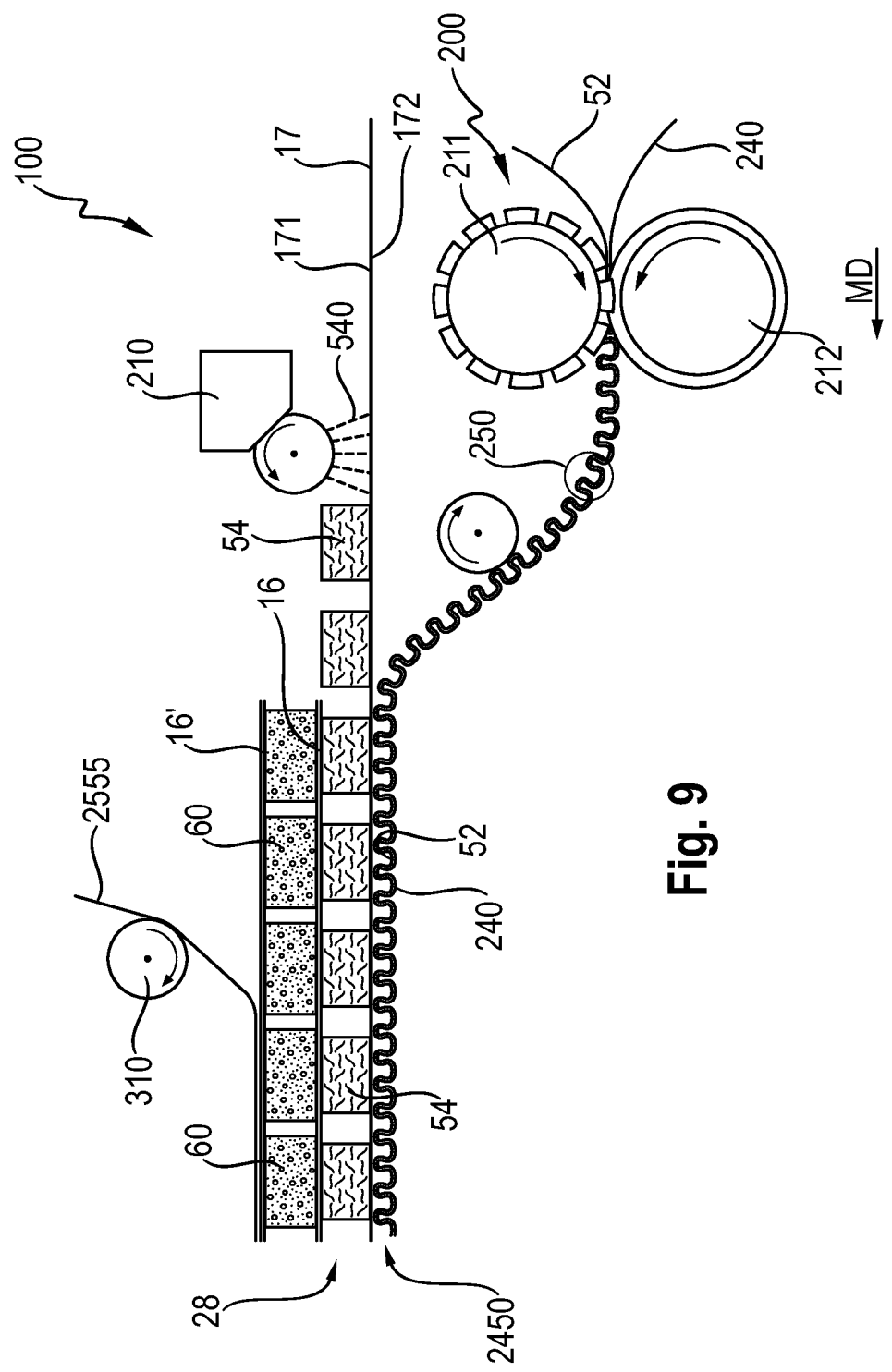
FIG. 9 is a side schematic view of another example of a process according to the present invention.
Figure 10:
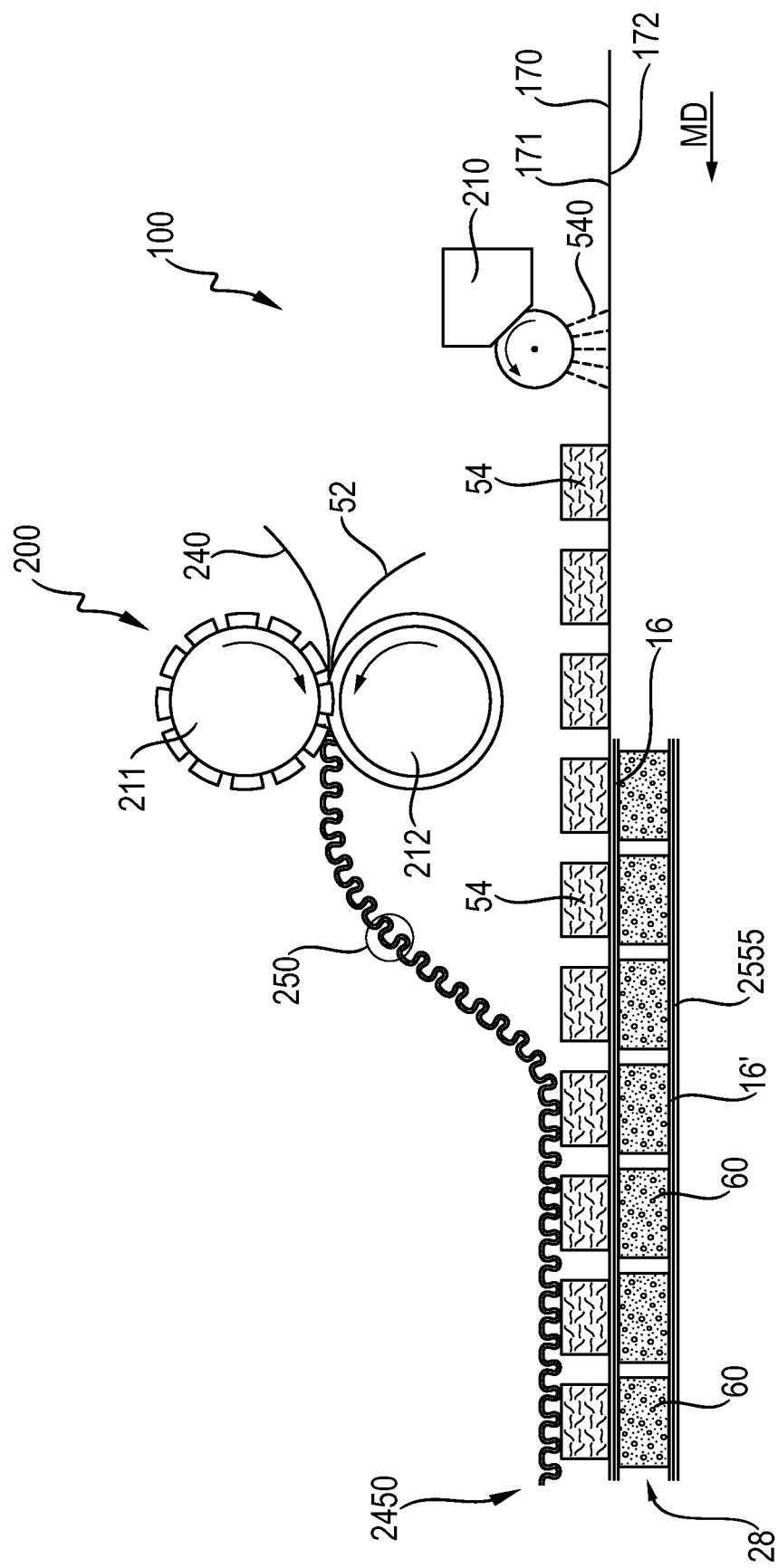
FIG. 10 is a side schematic view of another example of a process according to the present invention.

A process of making an absorbent article comprises the step of providing a liquid permeable topsheet web 240 extending substantially continuously in a machine direction, the topsheet web 240 having a first and second surface, a liquid impermeable backsheet web 2555 extending substantially continuously in the machine direction, an acquisition layer 52 having a first and second surface, a dry-laid fibrous structure and a carrier layer web 170 having a first and second surface (171, 172), as shown in FIGS. 9 and 10. The topsheet web 240 and the acquisition layer 52 comprise fibers.

The topsheet web 240 and acquisition layer 52 are aligned in a face to face relationship with the acquisition layer 52 such that the second surface of the topsheet web 240 is in contact with the first surface of the acquisition layer 52. The topsheet web 240 and the acquisition layer 52 are simultaneously mechanically deformed and combined together. The topsheet 24 and acquisition layer 52 are nested together such that the majority of the three-dimensional protrusions formed in the topsheet 24 coincide with and fit together with the majority of the three-dimensional protrusions formed in the acquisition layer 52 to provide a topsheet/acquisition layer laminate 245 having three-dimensional protrusions 250 The width of the acquisition layer 52 is less that the width of the topsheet 24 in a cross direction. The topsheet/ acquisition layer laminate 245 has a first surface comprising the second surface of the acquisition layer 52.

The dry-laid fibers 540 of the dry-laid fibrous structure are deposited on the first surface 171 of the carrier layer web 170 as shown in FIGS. 9 and 10. A portion of the backsheet web 2555 is joined to a portion of the topsheet web 240 of the topsheet/acquisition layer laminate web 2450 such that the second surface 172 of the carrier layer web 170 is facing the topsheet/acquisition layer laminate web 2450 or the backsheet web 2555.

Hence, the carrier layer web 170 can carry out the material of the distribution layer 54 wherever the topsheet/acquisition layer laminate web 2450 is produced and provided in the process.

According to the method used for making the three-dimensional structure of the topsheet/acquisition layer laminate web 2450, when the topsheet web 240 and acquisition layer 52 are mechanically deformed together, holes might unintentionally occur. When the distribution layer 54 comprises the dry-laid fibrous structure, the dry-laid fibers 540 of the dry-laid fibrous structure may pass through the unintentional holes at the resulting topsheet/acquisition layer laminate 245 and contact undesirably the skin of the wearer. It may be desirable to prevent that dry-laid fibers 540 of the dry-laid fibrous structure can pass through the unintentional holes of the resulting topsheet/acquisition layer laminate 245.

Figure 11:
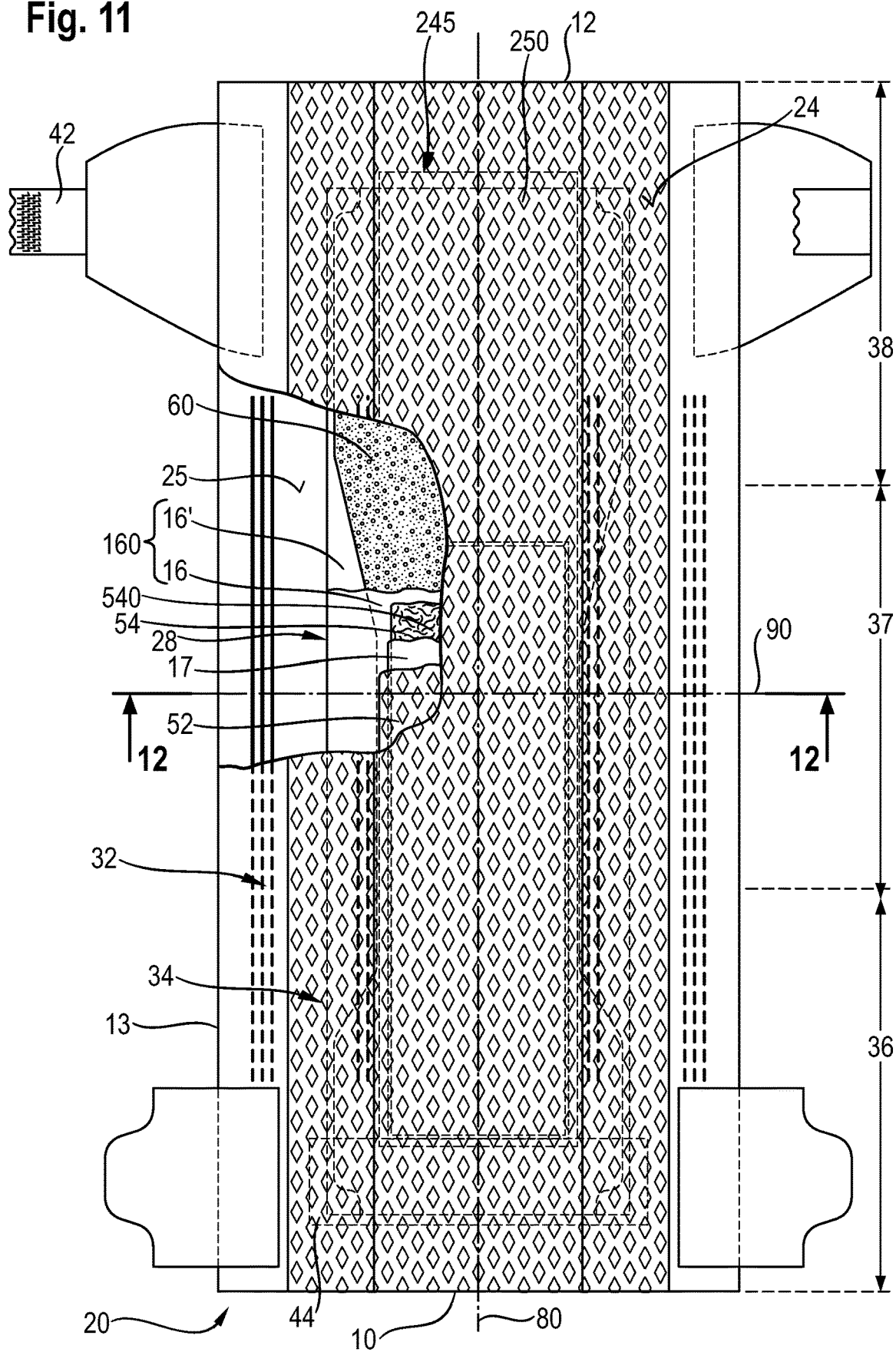
FIG. 11 is an absorbent article in the form of a diaper comprising an exemplary topsheet/acquisition layer laminate with a carrier layer according to the present invention with some layers partially removed.
Figure 12B:
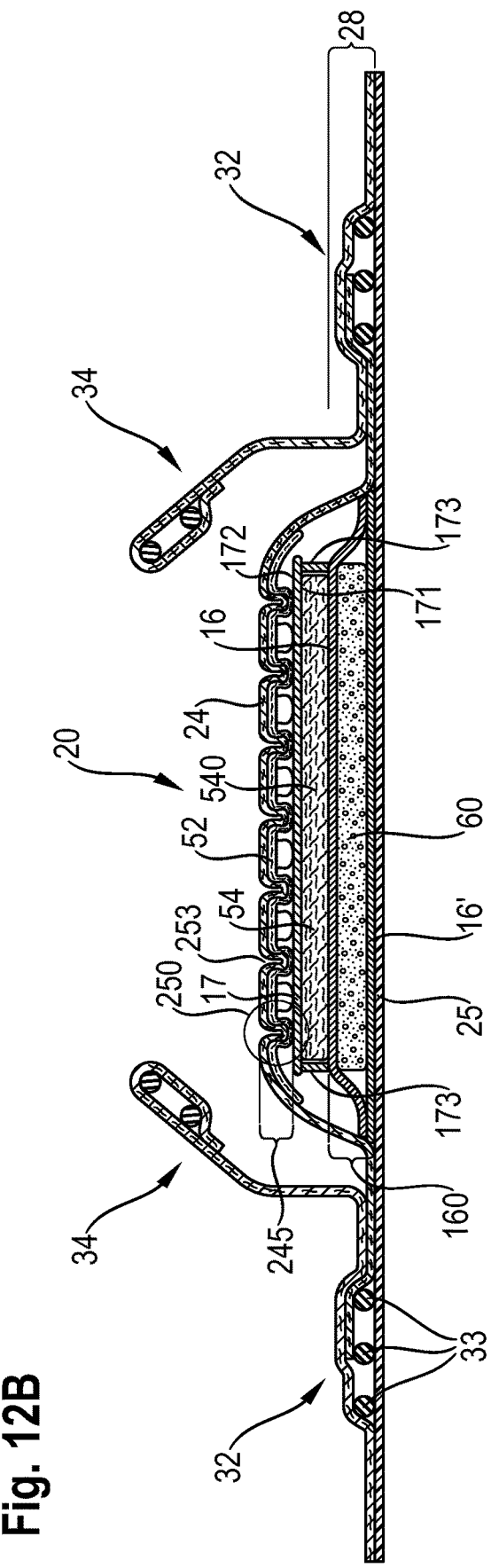
FIG. 12B is another transversal cross-section of the diaper of FIG. 11.

The carrier layer web 170 may be disposed between the topsheet/acquisition layer laminate web 2450 and the dry-laid fibrous structure, as shown in FIG. 9. In the absorbent article 20, the carrier layer 17 may act as a barrier layer to impede the dry-laid fibers 540 of the dry-laid fibrous structure from passing through the holes of the topsheet/acquisition layer laminate 245 unintentionally formed by the three-dimensional mechanical deformation of the topsheet 24 with the acquisition layer 52, as shown in FIGS. 11 and 12(A-B). Also, the carrier layer 17 may help the transfer of the liquid bodily exudates from the topsheet/acquisition layer laminate 245 to the dry-laid fibrous structure.

The first surface 171 of the carrier layer 17 in the absorbent article 20 may be attached at or adjacent to its longitudinal edges to the absorbent core 28. Hence, when the carrier layer 17 is disposed between the topsheet/acquisition layer laminate 245 and the dry-laid fibrous structure, and first surface 171 of the carrier layer 17 is attached to the absorbent core 28, the dry-laid fibers 540 of the dry-laid fibrous structure may be not able to escape between the carrier layer 17 and the absorbent core 28, as exemplified in FIG. 12B. The attachment of the carrier layer 17 to the longitudinal edges of the absorbent core 28 may include a uniform continuous layer of adhesive 173, a discontinuous patterned application of adhesive or an array of separate lines, spirals, or spots of adhesive.

Figure 13:
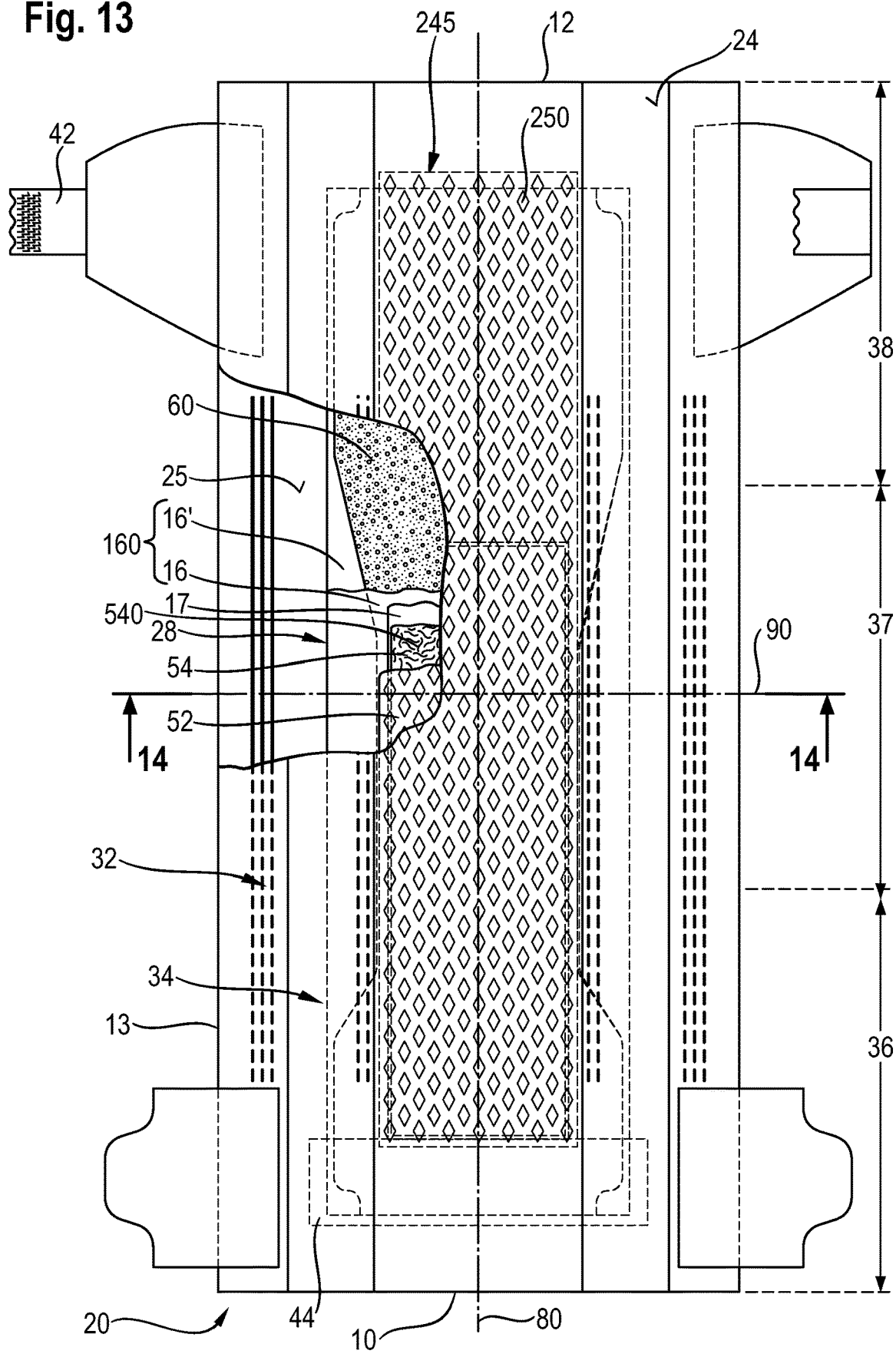
FIG. 13 is an absorbent article in the form of a diaper comprising an exemplary topsheet/acquisition layer laminate with a carrier layer according to the present invention with some layers partially removed.
Figure 14:
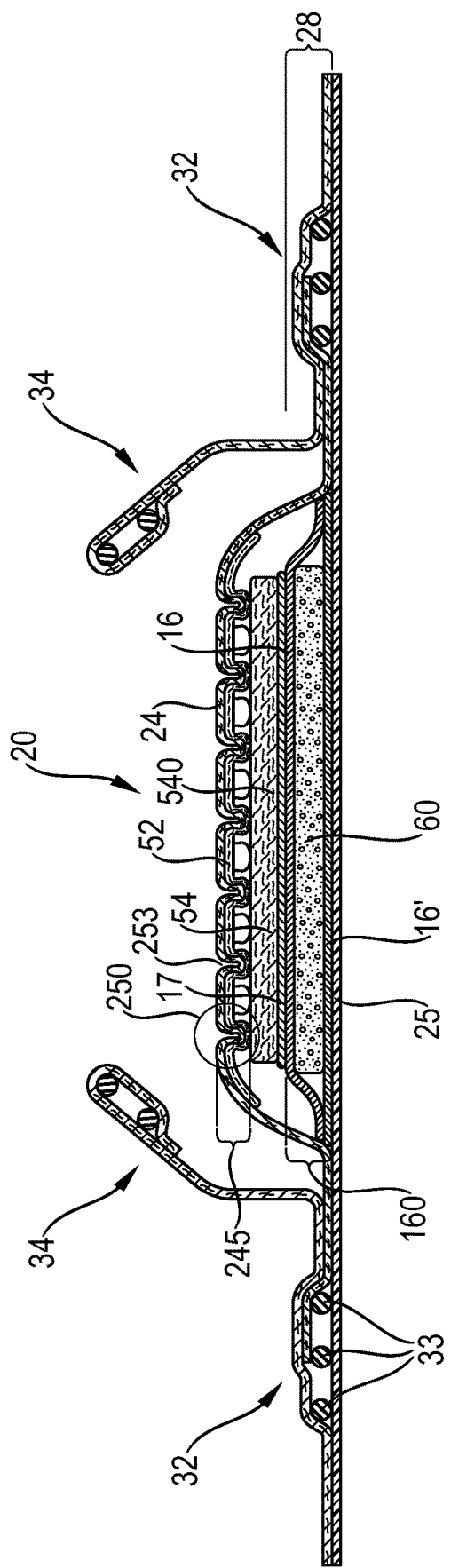
FIG. 14 is a transversal cross-section of the diaper of FIG. 13.

Alternatively, the carrier layer web 170 may be disposed between the dry-laid fibrous structure and the absorbent core 28, as shown in FIG. 10. Hence, the carrier layer 17 in the absorbent article 20 may help to distribute and transfer of the liquid bodily exudates from the distribution layer 54 to the absorbent core 28, as shown in FIGS. 13 and 14, which enables more efficient use of the absorbent core 28.

The carrier layer 17 may be attached at or adjacent to its longitudinal edges to the first surface of the topsheet/acquisition layer laminate 245. Hence, when the carrier layer 17 is disposed between the dry-laid fibrous structure and the absorbent core 28, and the carrier layer 17 is attached to the first surface of the topsheet/acquisition layer laminate 245, the dry-laid fibers 540 of the dry-laid fibrous structure may be not able to escape between the topsheet/acquisition layer laminate 245 and the carrier layer 17. The attachment of the carrier layer 17 to the longitudinal edges to the first surface of the topsheet/acquisition layer laminate 245 may include a uniform continuous layer of adhesive, a discontinuous patterned application of adhesive or an array of separate lines, spirals, or spots of adhesive.

The process may comprise the step of cutting into individual absorbent articles 20 comprising a backsheet 25, a carrier layer 17, a topsheet 24 and an acquisition layer 52 characterized in that the topsheet 24 and acquisition layer 52 are joined to form a topsheet/acquisition layer laminate 245.

The acquisition layer 52 of the topsheet/acquisition layer laminate web 2450 may be provided continuously in the machine direction. A length of the acquisition layer 52 of the topsheet/acquisition layer laminate 245 in a direction parallel to the longitudinal axis 80 may be equal of a length of the topsheet 24 in a direction parallel to the longitudinal axis 80.

Alternatively, the acquisition layer 52 of the topsheet/acquisition layer laminate web 2450 may be provided intermittently in the machine direction. The length of the acquisition layer 52 of the topsheet/acquisition layer laminate 245 in a direction parallel to the longitudinal axis 80 may be less than the length of the topsheet 24 in a direction parallel to the longitudinal axis 80, as shown in FIG. 1. When the length of the acquisition layer 52 in the topsheet/acquisition layer laminate 245 is less than the length of the topsheet 24, the liquid bodily exudates cannot be readily drawn towards the longitudinal edges (10, 12) of the absorbent article 20, which reduces leakage.

Figure 15:
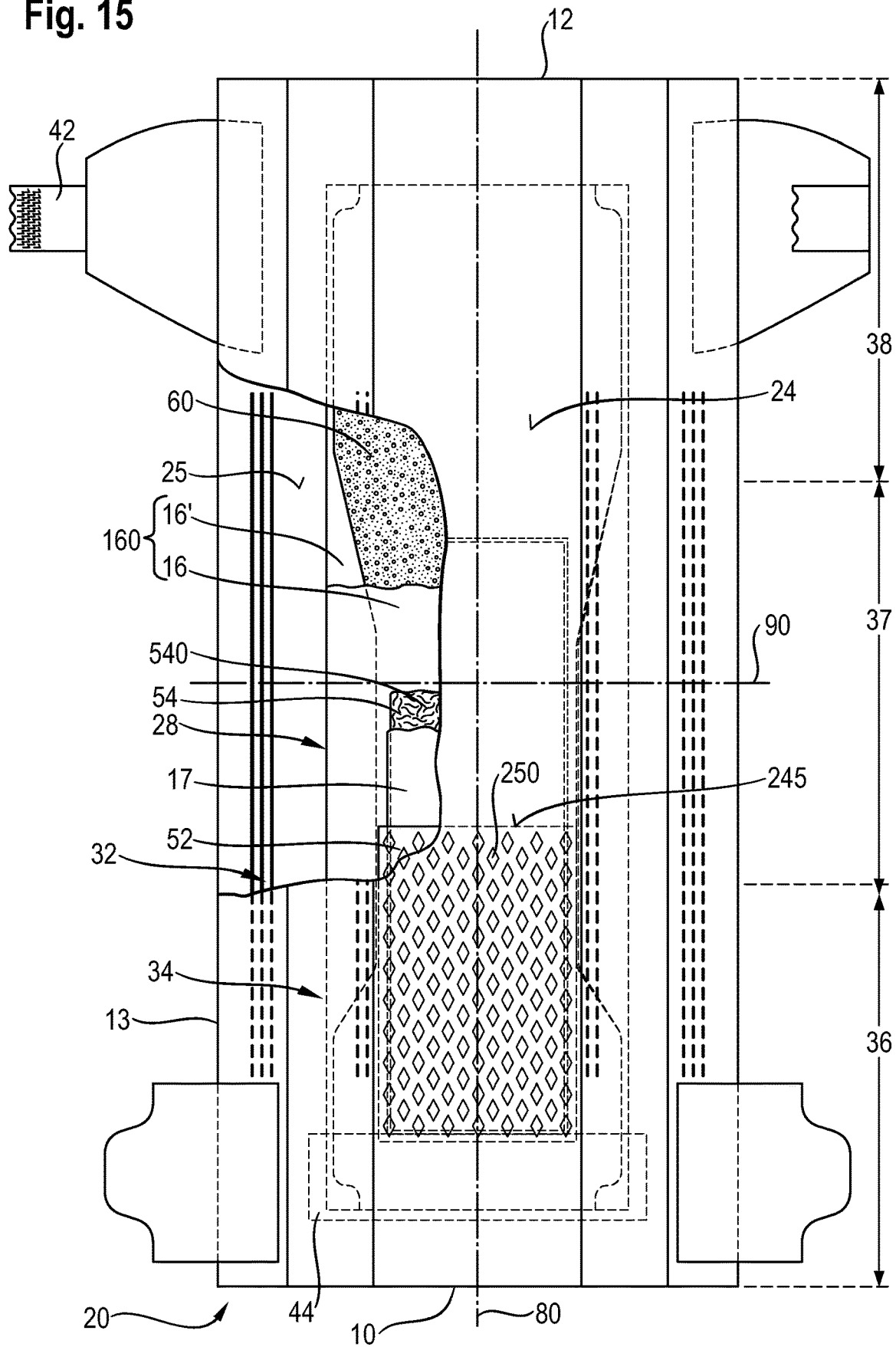
FIG. 15 is an absorbent article in the form of a diaper comprising an exemplary topsheet/acquisition layer laminate with an acquisition layer positioned in a front region of the absorbent article according to the present invention with some layers partially removed.

The acquisition layer 52 of the topsheet/acquisition layer laminate 245 may be positioned in the front region 36 and at least partially in the crotch region 37 of the absorbent article 20, as shown in FIG. 15. In that case, positioning the acquisition layer 52 of the topsheet/acquisition layer laminate 245 in the front region 36 of the absorbent article 20 helps for acquiring and distributing the liquid bodily exudates such as urine, around the pee point of the wearer.

Figure 16:
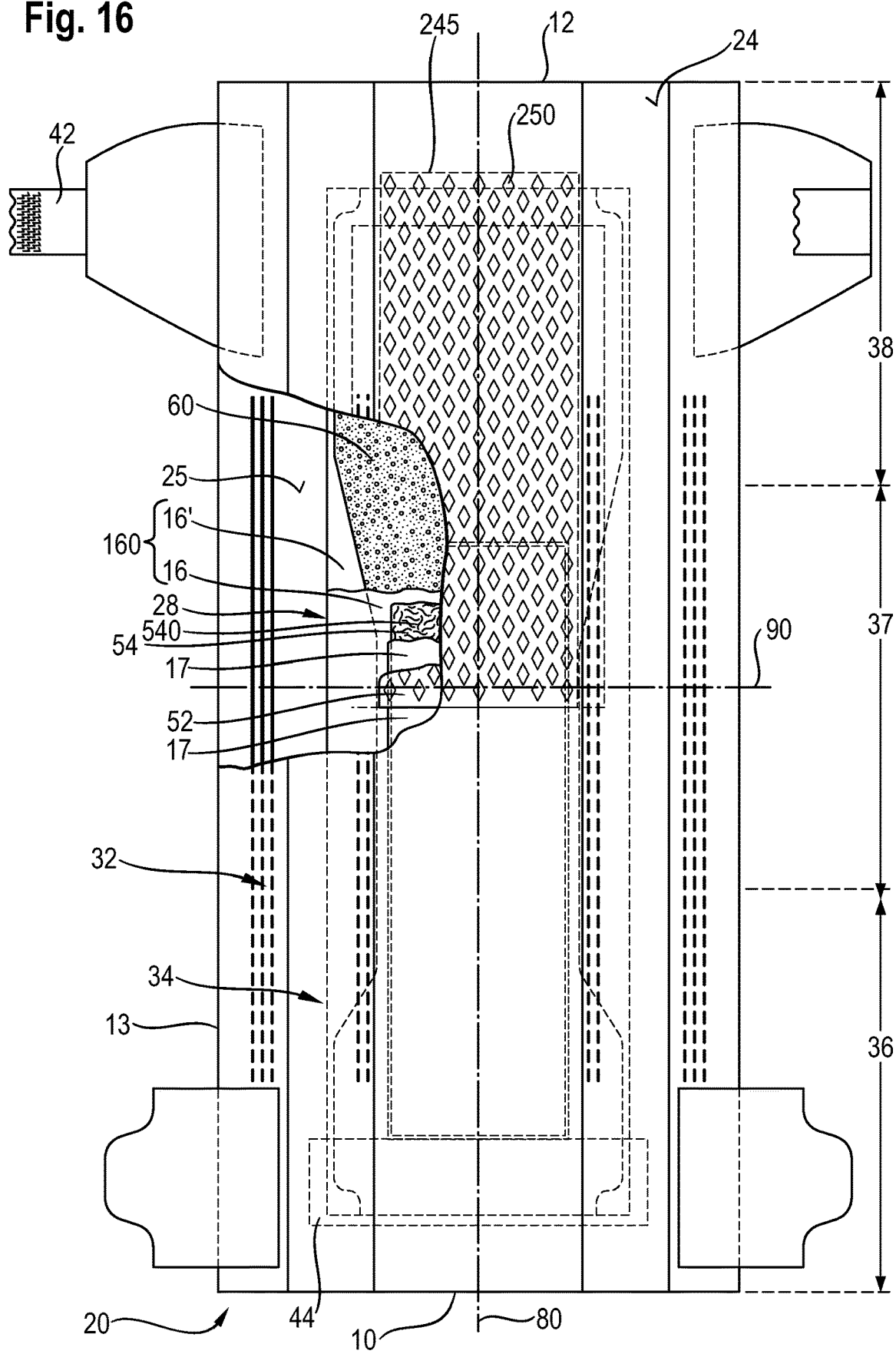
FIG. 16 is an absorbent article in the form of a diaper comprising an exemplary topsheet/acquisition layer laminate with an acquisition layer positioned in a rear region of the absorbent article according to the present invention with some layers partially removed.

The acquisition layer 52 of the topsheet/acquisition layer laminate 245 may be positioned in the back region 38 and at least partially in the crotch region 37 of the absorbent article 20, as shown in FIG. 16. Positioning the acquisition layer 52 of the topsheet/acquisition layer laminate 245 in the back region 38 of the absorbent article 20 helps at acquiring the feces of the wearer, especially when the feces have a low viscosity.

The majority of the three-dimensional protrusions 250 of the topsheet/acquisition layer laminate 245 may protrude toward the backsheet 25 or towards the body of the wearer when the absorbent article is in use.

The majority of the three-dimensional protrusions 250 may form, in conjunction, one or more graphics. Having graphics can support the caregiver's perception that the absorbent article is well able to absorb the liquid bodily exudates.

Also, the majority of the three-dimensional protrusions 250 may form, in conjunction, one or more graphics such as a logo, e.g. the Pampers Heart logo.

The topsheet/acquisition layer laminate 245 may be notionally divided into a first and second area. The first area may comprise three-dimensional protrusions 250 which protrude towards the backsheet 25. The second area may comprise three-dimensional protrusions 250 which protrude towards the body of the wearer when the absorbent article is in use.

For instance, the first area may be located in the front region 36 and at least partially in the crotch region 37 of the absorbent article 20.

Having the first area where the three-dimensional protrusions 250 of the topsheet/acquisition layer laminate 245 protrude towards the backsheet 25 can help acquiring and absorbing the liquid bodily exudates to the absorbent core 28. Having the second area where the three-dimensional protrusions 250 of the topsheet/acquisition layer laminate 245 protrude towards the body of the wearer when the absorbent article is in use can improve cleaning the body from the exudates. Hence, a combination of the first and second area can allow the absorbent article 20 to better perform.

The topsheet 24 of topsheet/acquisition layer laminate 245 may be coated with a lotion composition. The lotion composition may be located in the areas of the topsheet 24 which are between the three-dimensional protrusions 250 of the topsheet/acquisition layer laminate 245.

Typical lotion compositions used in diapers are disclosed in U.S. Pat. No. 6,426,444 B2. The resulting lotion composition may be applied to the topsheet/acquisition layer laminate by spraying, printing (e.g., flexographic printing), coating (e.g., contact slot coating, gravure coating), extrusion, microencapsulation or combinations of these application techniques.

The majority of the three-dimensional protrusions 250 may be disposed in any suitable arrangement across the plane of the topsheet/acquisition layer laminate 245. Suitable arrangements include, but are not limited to: staggered arrangements, and zones. In some cases, the topsheet/acquisition layer laminate 245 may comprise both three-dimensional protrusions 250 and other features known in the art such as embossments and apertures. The three-dimensional protrusions 250 and other features may be in separate zones, be intermixed, or overlap. Intermixed arrangements can be created in any suitable manner. In some cases, intermixed arrangements can be created by using the techniques described in U.S. Patent Publication No. US 2012/0064298 A1, Orr, et al. In other cases, overlapping arrangements can be created by forming the three-dimensional protrusions 250 and then subsequently passing the topsheet/acquisition layer laminate web 2450 between a forming member having male forming elements thereon and a compliant surface, and applying pressure to the web with the forming member and compliant surface. These techniques for producing overlapping arrangements enable three-dimensional protrusions 250 and other features to be combined so they are disposed in different locations on the topsheet/acquisition layer laminate 245 or they can cause at least some of the three-dimensional protrusions 250 and at least some of the other features (apertures, embossments) to be disposed in the same location on the topsheet/acquisition layer laminate 245.

The Carrier Layer

The carrier layer 17 may be selected from the group consisting of nonwovens, tissues, or films and combinations thereof.

Examples of a nonwoven web used for the carrier layer 17 may include various types of known nonwoven webs such as a spunbonded nonwoven web, a meltblown nonwoven web, and a spunbond-meltblown-spunbond nonwoven web. These nonwoven webs are made of thermoplastic polymers.

A material for fibers composing the nonwoven web used for the carrier layer 17 may include various types of known fibers such as polyethylene, polypropylene, polyester, and acryl, conjugate fibers such as polyethylene/polypropylene, polyethylene/polyethylene terephthalate, and polypropylene/polyethylene terephthalate, i.e., fibers formed of core-in-sheath fibers and side-by-side fibers. The fibers may be used alone or in combination. Further, the carrier layer 17 may have a monolayer structure or a multilayer structure.

The carrier layer 17 may comprise a tissue made of wet-laid fibers comprising cellulose fibers having a Wet burst Strength from 50 to 500 g according to the Wet Burst Strength Test Method and combinations thereof.

The carrier layer 17 may be treated with a surfactant to render the carrier layer 17 hydrophilic. The carrier layer 17 may be made of one material of the group as set out above, which has been chemically modified to render it hydrophilic. The hydrophilic carrier layer 17 may thus improve the transfer of the liquid bodily exudates from the distribution layer 54 to the absorbent core 28 of the absorbent article 20.

The carrier layer 17 may have a basis weight of at least 5 gsm to 60 gsm or at least 5 gsm to 20 gsm or at least 5 to 15 gsm.

The carrier layer 17 may be colored. The process may comprise the step of providing a carrier layer which is colored. Color may be imparted to the carrier layer 17 by color pigmentation. The term "color pigmentation" encompasses any pigments suitable for imparting a non-white color to the carrier layer 17. This term therefore does not include "white" pigments such as $TiO_2$ which are typically added to the layers of conventional absorbent articles to impart them with a white appearance. Pigments are usually dispersed in vehicles or substrates for application, as for instance in inks, paints, plastics or other polymeric materials.

The pigments may for example be introduced in a polypropylene masterbatch. A masterbatch comprises a high concentration of pigment and/or additives which are dispersed in a carrier medium which can then be used to pigment or modify the virgin polymer material into a pigmented bicomponent nonwoven. An example of suitable colored masterbatch material that can be introduced is Pantone color 270 Sanylen violet PP 42000634 ex Clariant, which is a PP resin with a high concentration of violet pigment. Typically, the amount of pigments introduced by weight of the carrier layer 17 may be of from 0.3%-2.5%.

Alternatively, color may be imparted to the carrier layer 17 by way of impregnation of a colorant into the substrate. Colorants such as dyes, pigments, or combinations may be impregnated in the formation of substrates such as polymers, resins, or nonwovens. For example, the colorant may be added to molten batch of polymer during film, fiber, or filament formation.

When viewing the absorbent article 20 from the topsheet 24, the colored carrier layer 17 may provide to a caregiver an enhanced impression of depth to support to the impression given by the three-dimensional protrusions 250 as such, as long as the colored carrier layer 17 are visible from the topsheet 24. Hence, a colored carrier layer 17 can support the caregiver's perception that the absorbent article 20 is well able to absorb the liquid bodily exudates.

The topsheet 24 and/or acquisition layer 52 of the topsheet/acquisition layer laminate 245 may be colored, for the same reasons.

The carrier layer 17 may be porous, may have a relatively high permeability and have a relatively high level of saturation when exposed to fluid at suction pressures such as 20 cm water. The relatively high level of saturation of the carrier layer 17 can be defined as the ratio between the volume of liquid bodily exudates in the pores of the carrier layer 17 and the total void volume of the carrier layer 17. The carrier layer 17 can help providing connectivity between the acquisition layer 52 of the topsheet/acquisition layer laminate 245 and the distribution layer 54.

Also, the carrier layer 17 may comprise some relative small sized holes such that the dry-laid fibers 540 of the dry-laid fibrous structure of the distribution layer 54 may partially pass through the holes of the carrier layer. Hence, the dry-laid fibers 540 of the dry-laid fibrous structure can entangle and contact the acquisition layer 52 of the topsheet/acquisition layer laminate 245. The carrier layer 17 may comprise holes having a size from 0.02 mm to 10 mm.

The Mechanical Deformations and the Resulted Three-Dimensional Protrusions

Figure 17:
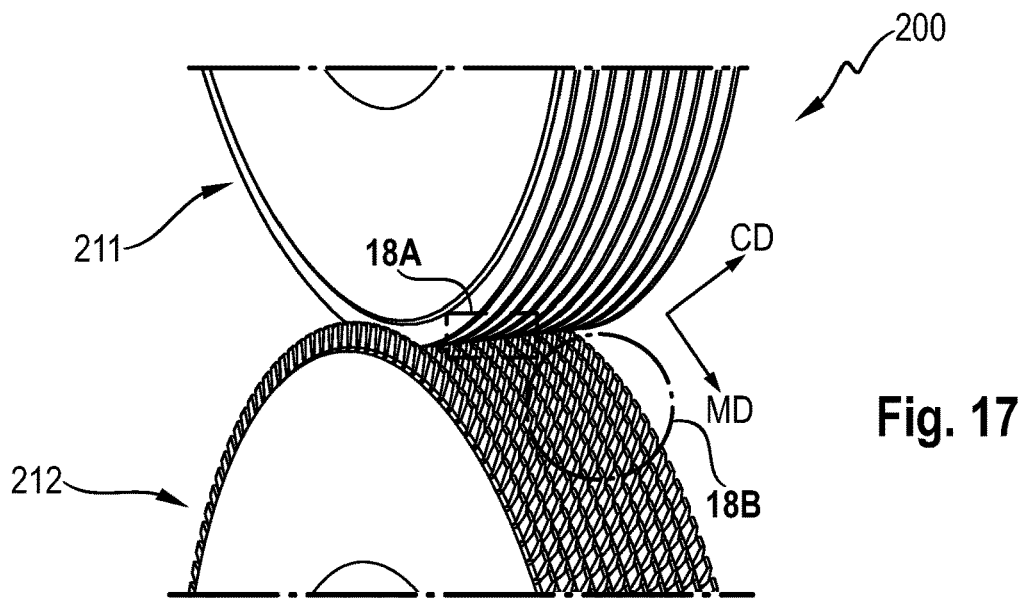
FIG. 17 is a perspective view of an apparatus comprising a first and second intermeshing roll for forming the topsheet/acquisition layer laminate web of the present invention.
Figure 18A:
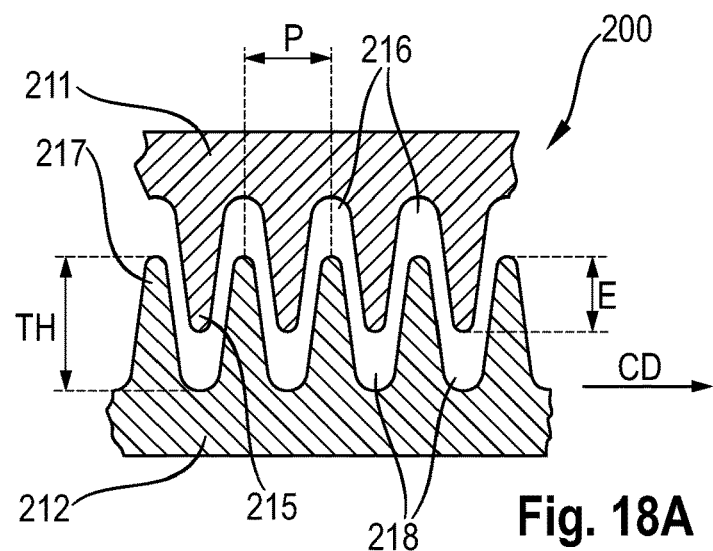
FIG. 18A is a cross-sectional depiction of a portion of the apparatus shown in FIG. 17.
Figure 18B:
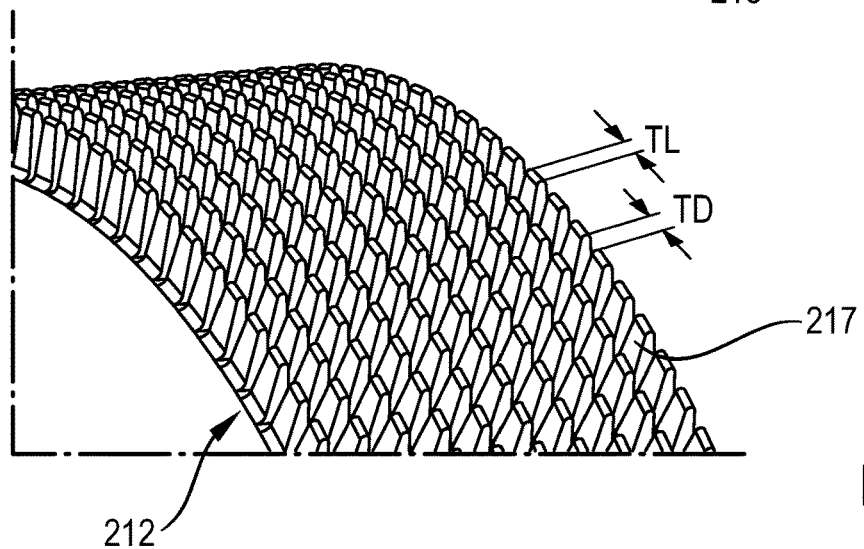
FIG. 18B is a perspective view of a portion of the second intermeshing roll of the apparatus shown in FIG. 17.

The step of the process 100 related to mechanically deforming and combining the topsheet 24 with the acquisition layer 52 may comprise the following step of providing a first and second intermeshing roll (211, 212) as shown in FIGS. 17, 18A and 18B.

The first intermeshing roll 211 of an apparatus 200 may comprise a plurality of ridges 215 and corresponding grooves 216 which extend unbroken substantially about a circumference of the first intermeshing roll 211.

The second intermeshing roll 212 may comprise a plurality of rows of circumferentially-extending ridges that have been modified to be rows of circumferentially-spaced teeth 217 and corresponding grooves 218, wherein the plurality of rows of circumferentially-spaced teeth 217 extend in spaced relationship about at least a portion of the second intermeshing roll 212.

The topsheet web 240 and acquisition layer 52 may be intermeshed together between the first and second intermeshing rolls (211, 212) such that the ridges 215 of the first intermeshing roll 211 extend into the grooves 218 of the second intermeshing roll 212 and the teeth 217 of the second intermeshing roll 212 extend into the grooves 216 of the first intermeshing roll 211 to form the topsheet/acquisition layer laminate 245. Hence, a plurality of deformations comprising three-dimensional protrusions 250 is obtained.

The three-dimensional protrusions 250 of the topsheet/acquisition layer laminate 245 may be only formed where the topsheet 24 overlaps the acquisition layer 52 in the topsheet/acquisition layer laminate 245.

The first and second intermeshing roll (211, 212) may be further defined by a tooth height TH, a pitch P and a depth of engagement E as shown in FIG. 18A. The tooth height TH may be measured from a surface of the second intermeshing roll 212 to a tip of a tooth 217. The tooth height TH may range from 0.5 mm to 10 mm or from 0.5 mm to 5 mm.

The pitch P may be defined as a tooth-to-tooth spacing which is measured from a tip of a first tooth to a tip of a second tooth of the second intermeshing roll 212. The first and second tooth of the second intermeshing roll 212 may be located in the cross-machine direction. The pitch P may range from 1 mm to 10 mm or from 1 mm to 5 mm.

The depth of engagement E is a measure of how much the first and second intermeshing rolls (211, 212) are engaging with each other. The depth of engagement E may be measured from a tip of a ridge 215 to a tip of a tooth 217 which is located next to the ridge 215 in the cross-machine direction. The depth of engagement E may range from 0.5 mm to 10 mm or from 0.5 mm to 5 mm or from 1 to 4 mm.

Each tooth 217 of the second intermeshing roll 212 may be defined by a circumferential tooth length TL and a tooth distance TD, as shown in FIGS. 17 and 18B. The circumferential tooth length TL may be measured from a leading edge to a trailing edge at a tooth tip. The tooth length TL may range from 0.5 mm to 10 mm or from 0.5 mm to 4 mm or from 1 mm to 4 mm.

Each tooth is separated from one another circumferentially by the tooth distance TD. The tooth distance TD may be measured from a leading edge of a first tooth to a trailing edge of a second tooth. The first and second teeth of the second intermeshing roll 212 may be on the same circumference in the machine direction. The tooth distance TD may range from 0.5 mm to 10 mm or from 0.5 mm to 5 mm or from 1 mm to 3 mm.

Other orientations of the teeth 217, grooves (216, 218) and ridges 215 may be possible, e.g. in CD direction versus MD direction.

The topsheet 24 and acquisition layer laminate are nested together such that the majority of the three-dimensional protrusions formed in the topsheet coincide with and fit together with the majority of the three-dimensional protrusions formed in the acquisition layer.

The topsheet 24 and acquisition layer 52 may be both extensible. The topsheet 24 and/or acquisition layer 52 may be able to stretch and do not interpenetrate through the respective ruptured topsheet or acquisition layer.

Generally, the extensibility of the materials composing the topsheet 24 and acquisition layer 52 can be selected according to the desired sizes of the three-dimensional protrusions 250. If relatively large three-dimensional protrusions 250 are desired, materials with a relatively higher extensibility will be chosen.

For instance, the topsheet 24 or acquisition layer 52 may be capable of undergoing an apparent elongation of equal to or greater than at least 100% or 110% or 120% or 130% up to 200% in the machine and/or cross-machine directions before reaching the breaking force according to the Test Method as set out in the Definition part.

In some cases, it might be desired to have three-dimensional protrusions 250 which are larger either in the machine or cross-machine direction. For this, the materials composing the topsheet 24 and acquisition layer 52 can be thus more extensible in either machine versus cross-machine direction or vice versa.

The topsheet/acquisition layer laminate 245 may comprise a plurality of three-dimensional protrusions 250. The plurality of three-dimensional protrusions 250 may protrude towards the distribution layer 54 (see also FIG. 2) or towards the carrier layer 17 (see FIGS. 11, 12). When the three-dimensional protrusions 250 extend towards the distribution layer 54, the area of contact between the acquisition layer 52 of the topsheet/acquisition layer laminate 245 and the underneath distribution layer 54 is improved. Hence, the transfer of the liquid bodily exudates from the topsheet/acquisition layer laminate 245 to the distribution layer 54 can be increased.

FIG. 19A-FIG. 19F shows different alternatives of three-dimensional protrusions 250. A loop-shaped protrusion may be one type of three-dimensional protrusions 250, see for example FIG. 19B. A loop-shaped protrusion may be obtained by the intermeshing process step as just described above using the apparatus 200.

Another type of three-dimensional protrusion 250 may be a tunnel-shaped loop. Generally, a tunnel-shape loop may comprise a base forming an opening and having a protrusion base width and also an opening at a leading edge 261 and an opening at a trailing edge 262, see for example FIG. 19C.

As shown in FIGS. 19A and 19B, a three-dimensional protrusion 250 in the form of a loop-shaped protrusion may comprise an inner and outer three-dimensional protrusion 251A and 251B. The inner three-dimensional protrusion 251A of the topsheet 24 is nested in the outer three-dimensional protrusion 251B of the acquisition layer 52.

The three-dimensional protrusion 250 may be made from intermeshing the topsheet 24 with the acquisition layer 52 such that the inner three-dimensional protrusions 251A of the topsheet 24 and the outer three-dimensional protrusions 251B of the acquisition layer 52 coincide with and fit together.

The inner three-dimensional protrusion 251A may comprise a plurality of looped fibers 254A of the topsheet 24. The outer three-dimensional protrusion 251B in which the inner three-dimensional protrusion 251A is nested, may comprise a plurality of looped fibers 254B of the acquisition layer 52.

The three-dimensional protrusion 250 may comprise a void area 253 which is the portion of the three-dimensional protrusion 251A which does not comprise any fibers. The three-dimensional protrusion 250 may be defined by a base 256 forming an opening proximate to the topsheet 24, a distal portion 257 and one or more side walls 255 between the base 256 and the distal portion 257. The three-dimensional protrusion 250 may be defined by a protrusion base width $WL_1$ of the base 256 forming an opening which is measured from two opposite side walls of the inner three-dimensional protrusion 251A at the base 256. Each three-dimensional protrusion 250 may be defined by a width $WL_2$ of the void area 253 which is the maximal width measured between two opposite side walls of the inner three-dimensional protrusion 251A. The width $WL_2$ of the void area 253 may be greater than the protrusion base width $WL_1$ of the base 256 of the three-dimensional protrusion 250. Measurements of the dimensions of the protrusion base width $WL_1$ of the base 256 and the width $WL_2$ of the distal portion 257 can be made on a photomicrograph. When the size of the protrusion base width $WL_1$ of the base 256 is specified herein, it will be appreciated that if the openings are not of uniform width in a particular direction, the protrusion base width, $WL_1$, is measured at the widest portion.

The majority of the three-dimensional protrusions 250 may have only one opening at the base 256. At least 50% or at least 80% of the three-dimensional protrusions 250 of the topsheet/acquisition layer laminate 245 may only have openings at the base 256. The majority of the three-dimensional protrusions 250 may be formed from the fibers of the topsheet 24 and the acquisition layer 52. The majority of the three-dimensional protrusions 250 may comprise a base 256 forming an opening, an opposed distal portion 257, and one or more side walls 255 between the bases 256 and the distal portions 257 of the three-dimensional protrusions 250. The base 256, distal portion 257 and the one or more side walls 255 may be formed by fibers such that the majority of the three-dimensional protrusions has only an opening at the base 256. The majority of the three-dimensional protrusions 250 may have a conical shape, see for example FIG. 19B.

As shown in FIG. 19C, each inner and outer three-dimensional protrusion (251A, 251B) may be made of a plurality of looped fibers (254A, 254B) which are aligned with one another in a machine direction and cross direction to create a tunnel-shaped loop 250 having openings (261, 262) on each extremity of the tunnel in addition to the opening at the base 256. In that case, the protrusion base width WL1 of the base 256 is relatively small. The measured protrusion base width $WL_1$ of the base 256 of the three-dimensional protrusion 250 may range from 0.1 mm to 1.2 mm or from 0.1 mm to 1 mm or from 0.1 mm to 0.5 mm according to the Protrusion Base Width Test Method.

In the area of the three-dimensional protrusions, the topsheet 24 and/or acquisition layer 52 may comprise one or more interruptions. The formation of the one or more interruptions may be due to the properties of the topsheet 24 and acquisition layer 52. The topsheet 24 may less extensible with regard to fiber mobility and/or fiber extensibility than the acquisition layer 52 or vice versa such that a hole starts to form in the topsheet 24 and/or acquisition layer 52.

Hence, as shown in FIG. 19D or 19E, the acquisition layer 52 may be interrupted in in the area of the three-dimensional protrusion 250 of the topsheet/acquisition layer laminate 245. The three-dimensional protrusion 251B of the interrupted acquisition layer 52 may comprise an interruption 258B.

Generally, the acquisition layer 52 may have a lower extensibility than the topsheet 24. In such cases, the acquisition layer 52 may start to rupture and form an interruption, i.e. the fibers composing the acquisition layer 52 may be less extensible and/or mobile than the fibers composing the topsheet 24.

The three-dimensional protrusion 251A of the non-interrupted topsheet 24 may coincide with and fit together with the three-dimensional protrusion 251B of the interrupted acquisition layer, as shown in FIG. 19D. In other words, the topsheet 24 is not pushed through the acquisition layer 52 such that the topsheet 24 does not interpenetrate through the acquisition layer 52.

Alternatively, the three-dimensional protrusion 251A of the non-interrupted topsheet 24 may partially fit together with the three-dimensional protrusion 251B of the interrupted acquisition layer 52, as shown in FIG. 19E.

Likewise, the topsheet 24 may be interrupted in the area of the three-dimensional protrusion 250 of the topsheet/ acquisition layer laminate 245.

Generally, the topsheet 24 may have a lower extensibility than the acquisition layer 52. In such cases, the topsheet 24 may start to rupture and form an interruption, i.e. the fibers composing the topsheet 24 may be less extensible and/or mobile than the fibers composing the acquisition layer 52.

In another alternative, the topsheet 24 and acquisition layer 52 may be interrupted in the area of the three-dimensional protrusions 250 of the topsheet/acquisition layer laminate 245 and the three-dimensional protrusions of the topsheet 251A coincide with and fit together with the three-dimensional protrusions 251B of the acquisition layer 52. The interruptions (258A) in the topsheet 24 in the area of the three-dimensional protrusions 250 of the topsheet/ acquisition layer laminate 245 will not coincide with the interruptions (258B) in the acquisition layer 52 in the area of the three-dimensional protrusions 250 of the topsheet/acquisition layer laminate 245, as shown in FIG. 19F.

The plurality of three-dimensional protrusions 250 may protrude towards the body of the wearer when the absorbent article 20 is in use (see also FIG. 3). When the three-dimensional protrusions 250 protrude towards the body of the wearer when the absorbent article 20 is in use, the area of contact between the topsheet 24 of the topsheet/acquisition layer laminate 245 and the wearer's skin is enhanced. Hence, the topsheet/acquisition layer laminate 245 provides cushioning to the wearer and an improved sensation of comfort.

FIG. 20A-FIG. 20D shows alternatives how a plurality of three-dimensional protrusions 250, e.g. loop-shaped protrusions, may protrude from the acquisition layer 52 to the topsheet 24 of the topsheet/acquisition layer laminate 245. In those alternatives, a three-dimensional protrusion 250 in the form of a loop-shaped protrusion may comprise an inner and outer three-dimensional protrusion 251A and 251B. The inner three-dimensional protrusion 251A of the acquisition layer 52 is nested in the outer three-dimensional protrusion 251B of the topsheet 24. The inner three-dimensional protrusion 251A may comprise a plurality of looped fibers 254B of the acquisition layer 52. The outer three-dimensional protrusion 251B in which the inner three-dimensional protrusion 251A is nested, may comprise a plurality of looped fibers 254A of the topsheet 24.

An area of 10 cm$^2$ of the topsheet/acquisition layer laminate 245 may comprise from 5 to 100 three-dimensional protrusions 250 from 10 to 50 three-dimensional protrusions 250 or from 20 to 40 three-dimensional protrusions 250.

Precursor Materials for the Topsheet and the Acquisition Layer

The topsheet/acquisition layer laminate 245 of the present invention can be made of any suitable nonwoven materials ("precursor materials"). In some cases, the topsheet/acquisition layer laminate 245 may also be free of cellulose materials. The precursor materials for the topsheet/acquisition layer laminate 245 may have suitable properties in order to be deformed. The suitable properties of the precursor materials may include: apparent elongation of the fibers, fiber mobility, ability to deform and stretch in the area where the three-dimensional protrusions 250 of the topsheet/acquisition layer laminate 245 are formed. Hence, the precursor materials are capable of undergoing mechanical deformation to ensure that the three-dimensional protrusion 250 will not tend to recover or return to the prior configuration of a flat topsheet 24 laminated on a flat acquisition layer 52.

Several examples of nonwoven materials suitable for use as a topsheet 24 for the topsheet/acquisition layer laminate 245 may include, but are not limited to: spunbonded nonwovens; carded nonwovens; and nonwovens with relatively specific properties to be able to be readily deformed.

One suitable nonwoven material as a topsheet 24 for the topsheet/acquisition layer laminate 245 may be an extensible polypropylene/polyethylene spunbonded nonwoven. One suitable nonwoven material as a topsheet 24 for the topsheet/acquisition layer laminate 245 may be a spunbonded nonwoven comprising polypropylene and polyethylene. The fibers may comprise a blend of polypropylene and polyethylene. Alternatively, the fibers may comprise bicomponent fibers, such as a sheath-core fiber with polyethylene on the sheath and polypropylene in the core of the fiber.

The topsheet 24 of the topsheet/acquisition layer laminate 245 may have a basis weight from 8 to 40 gsm or from 8 to 30 gsm or from 8 to 20 gsm.

Suitable nonwoven materials for the acquisition layer 52 of the topsheet/acquisition layer laminate 245 may include, but are not limited to: spunbonded nonwovens, through-air bonded ("TAB") carded high loft nonwoven materials, spunlace nonwovens, hydroentangled nonwovens, and resin bonded carded nonwoven materials. Spunbonded PET may be denser than carded nonwovens, providing more uniformity and opacity. Since PET fibers are not very extensible, the nonwoven can be bonded such that at least some of the fibers can be separated easily from the bond sites to allow the fibers to pull out of the bond sites and rearrange when the material is strained. This type of bonding, e.g. pressure bonding can help increasing the level of mobility of the fibers. Indeed, the fibers tend to pull out from the bond sites under tension.

The acquisition layer exhibits a basis weight from 10 to 120 gsm or from 10 to 100 gsm or from 10 to 80 gsm.

The topsheet 24 and/or acquisition layer 52 may have a density from 0.01 to 0.4 g/cm$^3$ or from 0.01 to 0.25 g/cm$^3$ or from 0.04 to 0.15 g/cm$^3$.

The topsheet 24 and acquisition layer 52 may be joined together prior or during the mechanical deformation. If desired an adhesive, chemical bonding, resin or powder bonding, or thermal bonding between the topsheet 24 and acquisition layer 52 may be selectively utilized to bond certain regions or all of the topsheet 24 and acquisition layer 52 together. In addition, the topsheet 24 and acquisition layer 52 may be bonded during processing, for example, by carding the topsheet 24 of onto the acquisition layer 52 and thermal point bonding the combined layers.

Prior to any mechanical deformation, the topsheet 24 may be attached to the acquisition layer 52. For instance, the topsheet 24 may be attached to the acquisition layer 52 where the topsheet 24 and the acquisition layer 52 overlaps. The attachment of the topsheet 24 to the acquisition layer 52 may include a uniform continuous layer of adhesive, a discontinuous patterned application of adhesive or an array of separate lines, spirals, or spots of adhesive. The basis weight of the adhesive in the topsheet/acquisition layer laminate 245 may be from 0.5 to 30 gsm or from 1 to 10 gsm or from 2 to 5 gsm.

Example

The topsheet and the acquisition layer were attached to each other with a hot melt adhesive applied in form of spirals with a basis weight of 5 gsm. The acquisition layer was centered onto the topsheet with respect to the topsheet and placed 50 mm from the front MD edge of the topsheet. The topsheet and acquisition layer attached together form a composite web.

The topsheet and acquisition layer attached together have been simultaneously mechanically deformed by passing them between a pair of intermeshing rolls (211, 212), see for example FIG. 17. The topsheet of the topsheet/acquisition layer laminate was in contact with the first intermeshing roll 211. The acquisition layer of the topsheet/acquisition layer laminate was in contact with the second intermeshing roll 212. The ridges and grooves have a triangular shaped cross-section, as exemplified in FIG. 18A. The pitch P of the rolls is 0.100 inch (2.5 mm). The second intermeshing roll 212 has discrete teeth 217 arranged in a staggered pattern. The teeth 217 have a uniform circumferential length dimension TL of about 0.195 inch (4.9 mm), are uniformly spaced from one another circumferentially by a distance TD of 0.162 inch (4.1 mm), and have a tooth height TH of about 0.270 inch (10.6 mm). The long sides of the teeth have a side wall angle of about 5 degrees from vertical, and the leading and trailing edges of the teeth have vertical side walls. The first intermeshing roll 211 has continuous ridges 215 with a height of about 0.270 inch (10.6 mm). The topsheet attached to the acquisition layer was intermeshed between the first and second intermeshing roll (211, 212) at 0.135 inch (3.43 mm) depth of engagement (DOE).

The topsheet of the topsheet/acquisition layer laminate was a hydrophilic coated mono component high elongation spunbond polypropylene (HES PP) nonwoven material with a density of 0.11 g/cm$^3$. The mono component HES PP nonwoven material for the topsheet has an overall basis weight of 20 gsm. The mono component HES PP nonwoven material was first coated with a finish made of a fatty acid polyethylene glycol ester for the production of a permanent hydrophilic mono component HES PP nonwoven material. The topsheet of the topsheet/acquisition layer laminate had a width of 168 mm and a length of 488 mm.

The acquisition layer of the topsheet/acquisition layer laminate was a spunbond nonwoven with a basis weight of 60 gsm with a density of 0.13 g/cm$^3$. The acquisition layer comprises 7 denier PET/coPET (polyethylene terephthalate)

trilobal bicomponent fibers with a 70/30 ratio of PET/coPET which has been treated with a surfactant. The acquisition layer of the topsheet/acquisition layer laminate had a width of 90 mm and a length of 338 mm.

The carrier layer was a co-PET/PET tipped-trilobal bicomponent fibers with a 90/10 ratio of PET/coPET. The basis weight of the carrier layer was 17.7 gsm. The carrier layer had a width of 168 mm and a length of 250 mm.

Prototype Diapers for the Example

Diaper prototypes for the above Example were produced using Pampers Premium Care S4 (size 4) diaper commercially available in Russia from October 2011 to October 2012. Pampers Premium Care S4 (size 4) diaper comprises a topsheet, an acquisition layer beneath the topsheet, a distribution layer beneath the acquisition layer, an absorbent core between the distribution and a backsheet beneath the absorbent core. Diaper prototypes for the above Example were produced using Pampers Premium Care S4 (size 4) diaper.

The topsheet and acquisition layer attached together for each example were placed on top of a Pampers Premium Care S4 (size 4) from where the commercial topsheet and acquisition layer were removed while keeping the distribution layer in place. For each diaper prototype based on the above Example, the topsheet/acquisition layer laminate were placed on top of the distribution layer with the three-dimensional protrusions protruding towards the backsheet.

A hot melt adhesive in form of spirals with a basis weight of 5 gsm was applied on the surface of the carrier layer facing the acquisition layer of the topsheet/acquisition layer laminate. The acquisition layer front edge is placed 10 mm from the distribution layer front edge. The topsheet/acquisition layer laminate attached to the carrier layer was attached onto the distribution layer and the absorbent core with a hot melt adhesive applied all over the side of the carrier layer and the topsheet facing the distribution layer. The hot melt adhesive was applied in form of spirals with a basis weight of 5 gsm.

The three-dimensional protrusions of the topsheet/acquisition layer laminate were protruding towards the backsheet because the topsheet of the topsheet/acquisition layer laminate was in contact with the male roll, as set out above.

Each prototype diaper was compacted in a bag at an In Bag Stack Height, i.e. the total caliper of 10 bi-folded diapers, of 90 mm for 1 week. Then the bag was opened and the diapers out of the bag were conditioned at least 24 hours prior to any testing at 23° C.+/−2° C. and 50%+/−10% Relative Humidity (RH).

The measured protrusion height and the measured protrusion base width of the three-dimensional protrusions of the topsheet/acquisition layer laminate have been measured according to the respective Protrusion Height and Protrusion Base Width Test Methods (Table 1).

TABLE 1

Measurements of the protrusion height and protrusion base width of the three-dimensional protrusions

| Replicate | Measured Protrusion Height (mm) | Measured Protrusion Base Width (mm) |
|---|---|---|
| average | 1.40 | 2.0 |
| Standard deviation | 0.0 | 0.1 |

Test Methods

Wet Burst Test Method

The Wet Burst Strength as used herein is a measure of the ability of a fibrous structure to absorb energy, when wet and subjected to deformation with regard to the plane of the fibrous structure.

The wet burst strength of a fibrous structure (referred to as "sample" within this test method) is determined using an electronic burst tester and specified test conditions. The results obtained are averaged out of 4 experiments and the wet burst strength is reported for a fibrous structure 55 consisting of one single layer of wet-laid fibers.

Equipment

Apparatus: Burst Tester—Thwing-Albert Vantage Burst Tester or equivalent ball burst instrument where the ball moves downward during testing. Refer to manufacturer's operation and set-up instructions. The ball diameter is 1.59 cm and the clamp opening diameter is 8.9 cm.

Calibration Weights—Refer to manufacturer's Calibration instructions

Conditioned Room Temperature and Humidity controlled within the following limits for Laboratory testing:

Temperature: 23°±1° C.
Relative humidity: 50%±2%
Paper Cutter—Cutting board, 600 mm size
Scissors—100 mm, or larger
Pan—Approximate Width/Length/Depth: 240×300×50 mm, or equivalent
Distilled water at the temperature of the conditioned room used Sample Preparation The fibrous structure 55 may be unwound from the roll.

The samples to be tested are conditioned in the conditioned room for 24 hours immediately before testing. All testing occurs within the conditioned room.

Cut the samples so that they are approximately 228 mm in length and width of approximately 140 mm in width.

Operation

Set-up and calibrate the Burst Tester instrument according to the manufacturer's instructions for the instrument being used.

Holding the sample by the narrow edges, the center of the sample is dipped into a pan filled approximately 25 mm from the top with distilled water. The sample is left in the water for 4 (±0.5) seconds.

The excess water is drained from the sample for 3 (±0.5) seconds holding the sample in a vertical position.

The test should proceed immediately after the drain step.

The sample should have no perforations, tears or imperfections in the area of the sample to be tested. If it does, start the test over.

The sample is placed between the upper and lower rings of the Burst Tester instrument. The sample is positioned centered and flat on the lower ring of the sample holding device in a manner such that no slack in the sample is present.

The upper ring of the pneumatic holding device is lowered to secure the sample.

The test is started. The test is over at sample failure (rupture) i.e., when the load falls 20 g from the peak force. The maximum force value is recorded.

The plunger will automatically reverse and return to its original starting position.

The upper ring is raised in order to remove and discard the tested sample.

The procedure is repeated until all replicates have been tested.

Wet Burst Strength=sum of peak load readings/number of replicates tested    Calculation Report the Wet Burst results to the nearest gram.

Protrusion Base Width and Protrusion Height Test Methods

1) General Information

The Measured Protrusion Base Width and Measured Protrusion Height of the three-dimensional protrusions of the topsheet/acquisition layer laminate of an absorbent article are measured using a GFM Primos Optical Profiler instrument commercially available from GFMesstechnik GmbH, Warthestraße 21, D14513 Teltow/Berlin, Germany. Alternative suitable non-touching surface topology profilers having similar principles of measurement and analysis, can also be used, here GFM Primos is exemplified.

The GFM Primos Optical Profiler instrument includes a compact optical measuring sensor based on a digital micro mirror projection, consisting of the following main components:

a) DMD projector with 800×600 direct digital controlled micro-mirrors
b) CCD camera with high resolution (640×480 pixels)
c) Projection optics adapted to a measuring area of at least 30×40 mm
d) Recording optics adapted to a measuring area of at least 30×40 mm
e) A table tripod based on a small hard stone plate
f) A cold light source (an appropriate unit is the KL 1500 LCD, Schott North America, Inc., Southbridge, Mass.)
g) A measuring, control, and evaluation computer running ODSCAD 6.3 software Turn on the cold-light source. The settings on the cold-light source are set to provide a color temperature of at least 2800K.

Turn on the computer, monitor, and open the image acquisition/analysis software. In the Primos Optical Profiler instrument, select "Start Measurement" icon from the ODSCAD 6.3 task bar and then click the "Live Image button".

The instrument is calibrated according to manufacturer's specifications using calibration plates for lateral (X-Y) and vertical (Z). Such Calibration is performed using a rigid solid plate of any non-shiny material having a length of 11 cm, a width of 8 cm and a height of 1 cm. This plate has a groove or machined channel having a rectangular cross-section, a length of 11 cm, a width of 6.000 mm and an exact depth of 2.940 mm. This groove is parallel to the plate length direction. After calibration, the instrument must be able to measure the width and depth dimensions of the groove to within ±0.004 mm.

All testing is performed in a conditioned room maintained at 23±2° C. and 50+/−10% relative humidity. The surface to be measured may be lightly sprayed with a very fine white powder spray. Preferably, the spray is NORD-TEST Developer U 89, available from Helling GmbH, Heidgraben, Germany 2) Protrusion Base Width Test Method The topsheet/acquisition layer laminate is extracted from the absorbent article by attaching the absorbent article to a flat surface in a taut planar (i.e. stretched planar) configuration with the topsheet of the topsheet/acquisition layer laminate facing up. Any leg or cuff elastics are severed in order to allow the absorbent article to lie flat. Using scissors, two longitudinal cuts are made through all layers above the absorbent core (i.e. the core wrap) along the edges of the topsheet/acquisition layer laminate. Two transversal cuts are made through the same layers following the front and back waist edges of the absorbent article.

The topsheet/acquisition layer laminate and any other layers above the absorbent core are then removed without perturbing the topsheet/acquisition layer laminate. Freeze spray (e.g. CRC Freeze Spray manufactured by CRC Industries, Inc. 885 Louis Drive, Warminster, Pa. 18974, USA), or equivalent aid may be used to facilitate removal of the uppermost layers from the absorbent article. The topsheet/acquisition layer laminate is then separated from any other layers, including any carrier layer (e.g. a nonwoven carrier layer, a tissue layer), using freeze spray if necessary. If a distribution layer, e.g. a pulp containing layer is attached to the topsheet/acquisition layer laminate, any residual cellulose fibers are carefully removed with tweezers without modifying the acquisition layer.

The topsheet/acquisition layer laminate with three-dimensional protrusions (conditioned at a temperature of 23° C.±2° C. and a relative humidity of 50%±10% for at least 24 hours) namely "the specimen" is laid down on a hard flat horizontal surface with the body-facing side upward, i.e. the topsheet of the topsheet/acquisition layer laminate being upward. Ensure that the specimen is lying in planar configuration, without being stretched, with the specimen uncovered.

A nominal external pressure of 1.86 kPa (0.27 psi) is then applied to the specimen. Such nominal external pressure is applied without interfering with the topology profile measurement. Such an external pressure is applied using a transparent, non-shining flat Plexiglas® plate 200 mm by 70 mm and appropriate thickness (approximately 5 mm) to achieve a weight of 83 g. The plate is gently placed on top of the specimen, such that the center point of the Plexiglas® plate is at least 40 mm away from any folds, with the entire plate resting on the specimen. A fold corresponds to a part of the absorbent article (e.g. the topsheet/acquisition layer laminate) where the absorbent article has been folded for packaging purposes.

Two 50 mm×70 mm metal weights each having a mass of 1200 g (approximate thickness of 43 mm) are gently placed on the Plexiglas® plate such that a 70 mm edge of each metal weight is aligned with the 70 mm edges of the Plexiglas® plate. A metal frame having external dimensions of 70 mm×80 mm and interior dimensions of 42 mm×61 mm, and a total weight of 142 g (approximate thickness 6 mm), is positioned in the center of the Plexiglas® plate between the two end weights with the longest sides of the frame aligned with the longest sides of the plate.

If the specimen is smaller than 70×200 mm, or if a large enough area without a fold is not present, or if an area of interest is close to the edges of the specimen and can't be analyzed with the Plexiglas and weights settings described above, then the X-Y dimensions of the Plexiglas® plate and the added metal weights may be adjusted to reach a nominal external pressure of 1.86 kPa (0.27 psi) while maintaining a minimum 30×40 mm field of view. At least 10 complete three-dimensional protrusions of the specimen should be captured in the field of view of 30 mm×40 mm.

Position the projection head to be normal to the specimen surface (i.e. to the topsheet of the topsheet/acquisition layer laminate).

Adjust the distance between the specimen and the projection head for best focus.

In the Primos Optical Profiler instrument, turn on the button "Pattern" to make a red cross appear on the screen ross and a black cross appears on the specimen.

Adjust the focus control until the black cross is aligned with the red cross on the screen.

Adjust image brightness then capture a digitized image.

In the Primos Optical Profiler instrument, change the aperture on the lens through the hole in the side of the projector head and/or altering the camera "gain" setting on the screen. When the illumination is optimum, the red circle at the bottom of the screen labeled "I.O." will turn green.

Click on the "Measure" button.

The topology of the upper surface of the topsheet/acquisition layer laminate specimen is measured through the Plexiglas plate over the entire field of view 30 mm×40 mm. It is important to keep the specimen still stationary during this time in order to avoid blurring of the captured image. The image should be captured within the 30 seconds following the placement of the Plexiglas plate, metal weights and frame on top of the specimen.

After the image has been captured, the X-Y-Z coordinates of every pixel of the 40 mm×30 mm field of view area are recorded. The X direction is the direction parallel to the longest edge of the rectangular field of view, the Y direction is the direction parallel to the shortest edge of the rectangular field of view. The Z direction is the direction perpendicular to the X-Y plane. The X-Y plane is horizontal while the Z direction is vertical, i.e. orthogonal to the X-Y plane.

These data are smoothed and filtered using a polynomial filter (n=6), a median filter 11 pixels by 11 pixels, and a structure filter 81 pixels by 81 pixels. The polynomial filter (n=6) approximates the X-Y-Z coordinate surface with a polynomial of order 6 and returns the difference to the approximated polynomial. The median filter 11 pixels by 11 pixels divides the field of view (40 mm×30 mm) in X-Y squares of 11 pixels by 11 pixels. The Z coordinate of the pixel located at the center of a given 11 pixels by 11 pixels square will be replaced by the mean Z value of all the pixels of this given square. The structure filter 81 pixels by 81 pixels, removes the waviness of the structure and translates all the Z peak values belonging to the bottom surface of the Plexiglas plate to a top X-Y plane.

A Reference Plane is then defined as the X-Y plane intercepting the surface topology profile of the entire field of view (i.e. 30 mm×40 mm), 100 microns below this top X-Y plane. In the Primos Optical Profiler instrument, to measure the Material Area of the Reference Plane (Z=−0.1 mm), click on the button "Evaluate". Then, apply a pre-filtering routine including a polynomial filter (n=6), a median filter 11 by 11 and a structure filter (n=81) using the function "Filter". Save the image to a computer file with ".omc" extension.

The same above procedure is then executed on the topsheet/acquisition layer laminate with the garment-facing side upward (i.e. the acquisition layer of the topsheet/acquisition layer laminate being upward), the 40 mm×30 mm field of view being located at the exact same X-Y position of the topsheet/acquisition layer laminate.

The Empty Area of the reference plane can be defined as the area of the Reference Plane that is above the surface profile. The Empty Areas having boundaries strictly located inside the field of view area (i.e. 30 mm×40 mm) without crossing or overlapping with the boundaries of the field of view area (i.e. 40 mm×30 mm) are defined as Isolated Empty Area(s). The Measured Protrusion Base Width is defined for an Isolated Empty Area as the diameter of the biggest circle that can be inscribed inside a given Isolated Empty Area. This circle should only overlap with the Isolated Empty Area.

In the Primos Optical Profiler instrument, this can be done by clicking on "Draw circle" and drawing the biggest inscribed circle possible in a chosen Isolated Empty Area. Click on "Show sectional picture", the circle diameter can be measure via clicking on the extremity of the sectional picture profile and then clicking on "Horizontal distance" to obtain the Protrusion Base Width.

For both of the acquired and digitized images, the Protrusion Base Width of all the Isolated Empty Areas is determined. Then, the Measured Protrusion Base Width is calculated as the arithmetic average of the 6 biggest Protrusion Base Widths.

3) Protrusion Height Test Method

The topsheet/acquisition layer laminate is extracted from the absorbent article as described above in the Protrusion Base Width Test Method.

The topsheet/acquisition layer laminate specimen comprising three-dimensional protrusions is then conditioned and scanned under a pressure of 1.86 kPa (0.27 psi) with the body-facing side upward, i.e. the topsheet of the topsheet/acquisition layer laminate being upward as described above in the Protrusion Base Width Test Method.

After the image has been captured, the X-Y-Z coordinates of every pixel of the 40 mm×30 mm field of view area are recorded and smoothed/filtered as described above in the Protrusion Base Width Test Method. A reference plane is also defined as described above in the Protrusion Base Width Test Method.

In the Primos Optical Profiler instrument, to measure the Material Area of the Reference Plane (Z=−0.1 mm), click on the button "Evaluate". Then apply a pre-filtering routine including a polynomial filter (n=6), a median filter 11 by 11 and a structure filter (n=81) using the function "Filter". Save the image to a computer file with ".omc" extension.

The same above procedure set out in the Protrusion Base Width Test Method is then executed on the topsheet/acquisition layer laminate with the garment-facing side upward (i.e. the acquisition layer of the topsheet/acquisition layer laminate being upward), the 40 mm×30 mm field of view being located at the exact same X-Y position of the topsheet/acquisition layer laminate.

The Empty Area of the reference plane can be defined as the area of the Reference Plane that is above the surface profile. The Empty Area having boundaries strictly located inside the field of view area (i.e. 30 mm×40 mm) without crossing or overlapping with the boundaries of the field of view area (i.e. 40 mm×30 mm) are defined as Isolated Empty Area(s). The Protrusion Height is defined for an Isolated Empty Area as the distance between the minimum Z value of the points of the topsheet/acquisition layer laminate surface profile having X-Y coordinates located in this Isolated Empty Area, and the Z value of the top X-Y plane.

Click on "Draw N parallel lines" and draw a first segment parallel to the X axis of the field of view (direction of the longest dimension of the field of view) passing through the center of the Isolated Empty Area and extending outside the Isolated Empty Area boundaries. The center of the Isolated Empty Area corresponds to the middle of the segment parallel to the Y axis of the field of view and joining the biggest and smallest Y value of the Isolated Empty Area. Then input the "number" of lines to be drawn and set the "distance" between lines to 0.05 mm. Enough lines need to be drawn such to cover the entire Isolated Empty Area. Leave the averaging parameter to 0 then click "Ok". Then click on "Show sectional picture". Click on the point of the sectional picture profile having the minimum Z value and click on "Vertical distance" to obtain the Protrusion Height.

For both of the acquired and digitized images, the Protrusion Height of all the Isolated Empty Areas is determined. Then, the Measured Protrusion Height is calculated as the arithmetic average of the 6 biggest Protrusion Heights.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making an absorbent article comprising the steps of:
    providing a liquid permeable topsheet web extending substantially continuously in a machine direction, the topsheet web having a plurality of fibers, a first topsheet web surface and second topsheet web surface; a liquid impermeable backsheet web extending substantially continuously in the machine direction, and an intermediate layer comprising a plurality of fibers, left and right longitudinal edges, a first intermediate layer surface and second intermediate layer surface;
    aligning the topsheet web and the intermediate layer in a face to face relationship such that the second topsheet web surface is in contact with the first intermediate layer surface;
    mechanically deforming the topsheet web together and the intermediate layer to form three-dimensional protrusions wherein the topsheet web and intermediate layer are nested together such that a majority of the three-dimensional protrusions formed in the topsheet web coincide with and fit together with a majority of the three-dimensional protrusions formed in the intermediate layer to provide a topsheet/intermediate layer laminate web having three-dimensional protrusions, wherein the topsheet/intermediate layer laminate web having three dimensional protrusions is formed by interrupting the topsheet web or intermediate layer in the area of the three dimensional protrusions of the topsheet/intermediate layer laminate web, wherein the topsheet layer or intermediate layer comprise at least one interruption within a portion of the three-dimensional protrusions;
    wherein a width of the intermediate layer is less than a width of the topsheet web in a cross direction; the topsheet/intermediate layer laminate web having a first surface comprising the second surface of the intermediate layer; and
    joining a portion of the backsheet web to a portion of the topsheet web of the topsheet/intermediate layer laminate web such that the first surface of the topsheet/intermediate layer laminate web is facing towards the backsheet web.

2. The process of claim 1, further comprising the step of forming respective left and right longitudinal barrier cuff structures to the topsheet web, the barrier cuff structures having respective left and right proximal edges joined to the topsheet web and free distal edges, the proximal edges being disposed laterally outside the left and right longitudinal edges of the intermediate layer.

3. The process of claim 1, wherein the topsheet web is a spunbond nonwoven web.

4. The process of claim 1, wherein the intermediate layer is a spunlace nonwoven web.

5. The process of claim 3, wherein the intermediate layer is a spunlace nonwoven web.

6. The process of claim 1, wherein the intermediate layer is a carded nonwoven web.

7. The process of claim 6, wherein the intermediate layer is hydroentangled.

8. The process of claim 1, wherein the step of mechanically deforming the topsheet web and the intermediate layer occurs simultaneously.

9. A process of making an absorbent article comprising the steps of:
    (a) providing a liquid permeable topsheet web extending substantially continuously in a machine direction, the topsheet web having a first and second surface, a liquid impermeable backsheet web extending substantially continuously in the machine direction and an intermediate layer having a first and second surface; wherein the topsheet web and the intermediate layer comprise fibers;
    (b) aligning the topsheet web and the intermediate layer in a face to face relationship such that the second surface of the topsheet web is in contact with the first surface of the intermediate layer;
    (c) mechanically deforming and combining the topsheet web and the intermediate layer wherein the topsheet web and intermediate layer are nested together such that a majority of the three-dimensional protrusions formed in the topsheet web coincide with and fit together with a majority of the three-dimensional protrusions formed in the intermediate layer to provide a topsheet/intermediate layer laminate web having three-dimensional protrusion, wherein the topsheet layer or intermediate layer comprise at least one interruption within a portion of the three-dimensional protrusion, wherein a width of the intermediate layer is less than a width of the topsheet web in a cross direction; the topsheet/intermediate layer laminate web having a first surface comprising the second surface of the intermediate layer; and
    (d) joining a portion of the backsheet web to a portion of the topsheet web of the topsheet/intermediate layer laminate web such that the first surface of the topsheet/intermediate layer laminate web is facing towards the backsheet web.

10. The process of claim 9 comprising the steps of:
    (a) providing a dry-laid fibrous structure or a wet-laid fibrous structure;

(b) depositing the dry-laid fibrous structure or the wet-laid fibrous structure on the first surface of the topsheet/intermediate layer laminate web or on the backsheet web; and (c) joining a portion of the backsheet to a portion of the topsheet web of the topsheet/intermediate layer laminate web such that the dry-laid fibrous structure or the wet-laid fibrous structure is positioned between the topsheet/intermediate layer laminate web and the backsheet web.

11. The process of claim 9, wherein the topsheet web is a spunbond nonwoven web.

12. The process of claim 9, wherein the intermediate layer is a spunlace nonwoven web.

13. The process of claim 11, wherein the intermediate layer is a spunlace nonwoven web.

14. The process of claim 9, wherein the intermediate layer is a carded nonwoven web.

15. The process of claim 14, wherein the intermediate layer is hydroentangled.

16. The process of claim 9, further comprising the step of forming respective left and right longitudinal barrier cuff structures to the topsheet web, the barrier cuff structures having respective left and right proximal edges joined to the topsheet web and free distal edges, the proximal edges being disposed laterally outside the left and right longitudinal edges of the intermediate layer.

17. The process of claim 9, wherein the step of mechanically deforming the topsheet web and the intermediate layer occurs simultaneously.

* * * * *